US012606739B2

(12) United States Patent
Hitosugi

(10) Patent No.: US 12,606,739 B2
(45) Date of Patent: Apr. 21, 2026

(54) LUMINESCENT COMPOUND, METHOD FOR PRODUCING LUMINESCENT COMPOUND, LUMINESCENT COMPOSITION, LUMINESCENT THIN FILM AND LUMINESCENT PARTICLES

(71) Applicant: KONICA MINOLTA, INC., Tokyo (JP)

(72) Inventor: Shumpei Hitosugi, Inagi (JP)

(73) Assignee: Konica Minolta, Inc., Tokyo (JP)

( * ) Notice: Subject to any disclaimer, the term of this patent is extended or adjusted under 35 U.S.C. 154(b) by 792 days.

(21) Appl. No.: 17/919,015

(22) PCT Filed: Mar. 29, 2021

(86) PCT No.: PCT/JP2021/013342

§ 371 (c)(1),
(2) Date: Oct. 14, 2022

(87) PCT Pub. No.: WO2021/210377

PCT Pub. Date: Oct. 21, 2021

(65) Prior Publication Data

US 2023/0235217 A1 Jul. 27, 2023

(30) Foreign Application Priority Data

Apr. 15, 2020 (JP) ................................ 2020-072665

(51) Int. Cl.

| | |
|---|---|
| ***C09K 11/06*** | (2006.01) |
| ***C07D 471/06*** | (2006.01) |
| ***C07D 491/16*** | (2006.01) |
| ***C07D 495/06*** | (2006.01) |
| ***C07F 5/02*** | (2006.01) |
| ***C09B 57/00*** | (2006.01) |

(52) U.S. Cl.

CPC ............ *C09K 11/06* (2013.01); *C07D 471/06* (2013.01); *C07D 491/16* (2013.01); *C07D 495/06* (2013.01); *C07F 5/02* (2013.01); *C09B 57/00* (2013.01); *C09K 2211/1022* (2013.01)

(58) Field of Classification Search

CPC ......... C09B 57/08; C09B 57/00; C09K 11/06; C09K 2211/1022; C07F 5/02; C07D 47/06; C07D 49/16

See application file for complete search history.

(56) References Cited

FOREIGN PATENT DOCUMENTS

| | | | |
|---|---|---|---|
| JP | 2019-533737 | A | 11/2019 |
| WO | 2018/065502 | A1 | 4/2018 |

OTHER PUBLICATIONS

Notice of Reasons for Refusal issued in corresponding Japanese Patent Application No. 2022-515278, dated Aug. 27, 2024 (8 pages).

Christopher Kohl et al., "Towards Highly Fluorescent and Wafer-Soluble Perylene Dyes" Chem. Eur. J., 2004 vol. 10, pp. 5297-5310 (14 pages).

International Search Report issued in corresponding International Application No. PCT/JP2021/013342 mailed May 25, 2021 (6 pages).

International Preliminary Report on Patentability issued in corresponding International Application No. PCT/JP2021/013342 mailed Oct. 13, 2022 (12 pages).

*Primary Examiner* — C Melissa Koslow

(74) *Attorney, Agent, or Firm* — Osha Bergman Watanabe & Burton LLP

(57) ABSTRACT

A luminescent compound has a structure represented by a general formula (1),

General formula (1)

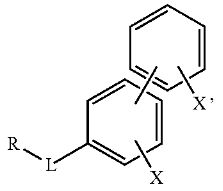

wherein R represents a luminescent dye skeleton, X represents an ionic substituent, and L represents a single bond, an oxygen atom, a sulfur atom, a selenium atom, or an NH group.

10 Claims, 1 Drawing Sheet

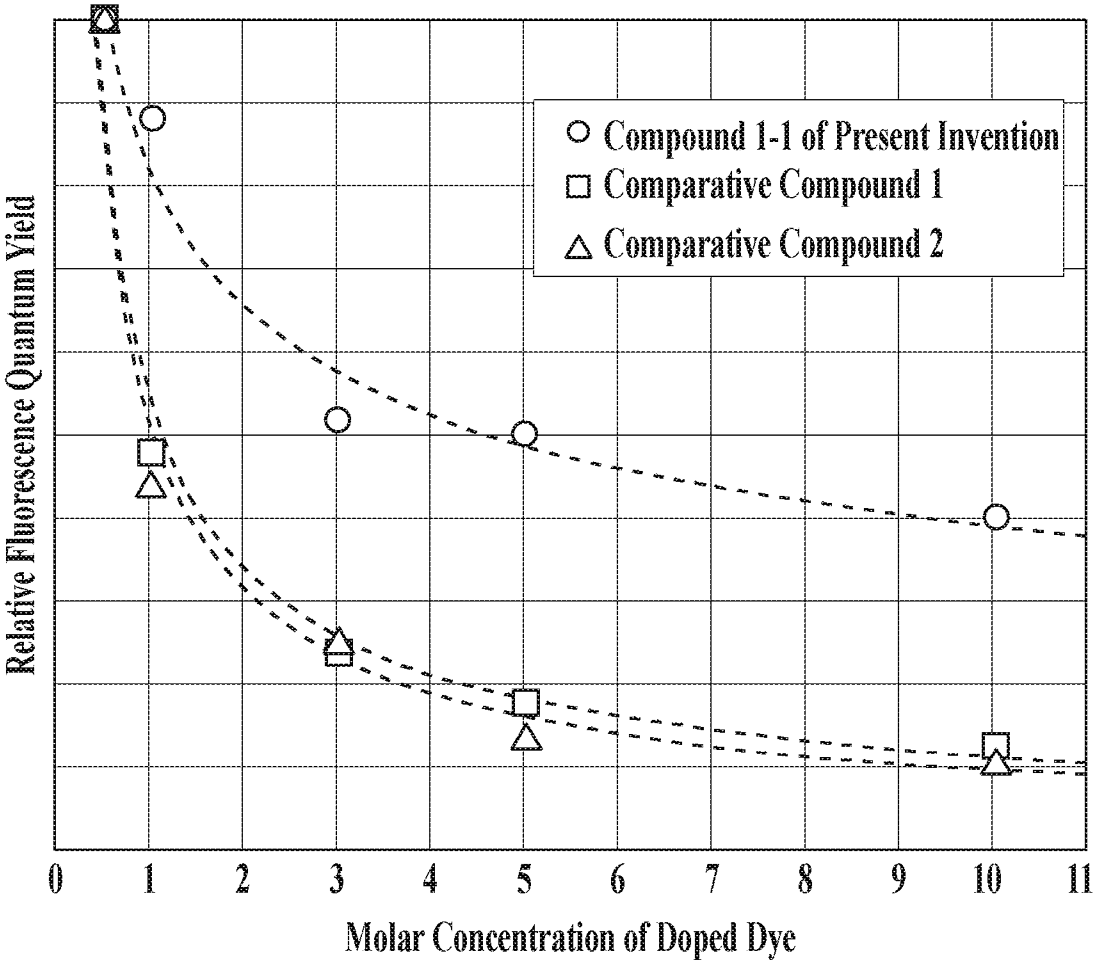
Compound 1-1 of Present Invention
Comparative Compound 1
Comparative Compound 2
Relative Fluorescence Quantum Yield
0
1
2
3
4
5
6
7
8
9
10
11
Molar Concentration of Doped Dye

LUMINESCENT COMPOUND, METHOD FOR PRODUCING LUMINESCENT COMPOUND, LUMINESCENT COMPOSITION, LUMINESCENT THIN FILM AND LUMINESCENT PARTICLES

TECHNOLOGICAL FIELD

Embodiments of the present invention relate to a luminescent compound, a method for producing a luminescent compound, a luminescent composition, a luminescent thin film, and a luminescent particle, and particularly to a luminescent compound having high water solubility and excellent luminescent properties due to a concentration quenching suppressing effect even under a high concentration condition.

BACKGROUND

Perylene bisimide derivatives are substances whose skeletons have been known at least as of 1995. Perylene bisimide derivatives are used as luminescent materials and the like because of their potentially high luminescence quantum yield, high fastness, ease of emission wavelength adjustment, simplicity of synthesis, and the like (see, for example, Patent Literature 1).

Perylene bisimide derivatives, which are polycyclic aromatic compounds having a wide π-conjugate plane, exhibit luminescence derived from π-π* transition, and exhibit high luminescence quantum yields in dilute solutions. On the other hand, however, when an aromatic compound originally having high fat-solubility is used as a water-soluble dye, there may be aggregation due to the hydrophobic effect of the core portion of the dye and a decrease in luminescence due to concentration quenching derived therefrom, and perylene bisimide derivatives have a defect that the luminescence quantum yield is significantly decreased in a high-concentration solution or in a solid state.

Therefore, for example, when a perylene bisimide derivative is used as a phosphor-integrated nanoparticle in an immunostaining method, some perylene bisimide derivative as a fluorescent dye is included in a small-diameter substance serving as a matrix or is attached to the surface to be integrated, so that luminescent properties are good. However, under high concentration conditions, the interaction between aromatic moieties having high lipid solubility of the dye particularly strongly acts due to a hydrophobic effect, and thus aggregation occurs, and there may be decrease in luminescence due to concentration quenching.

[Patent Literature 1] WO 2018/065502 A1

SUMMARY

One or more embodiments of the present invention provide a luminescent compound having high water solubility and excellent luminescent properties due to a concentration quenching suppressing effect even under a high concentration condition, a method for producing the same, and also to provide a luminescent composition, a luminescent thin film, and a luminescent particle containing the luminescent compound.

One or more embodiments of the present invention provide a luminescent compound or the like having high water solubility and capable of exhibiting a concentration quenching suppressing effect even under a high concentration condition by introducing a biphenyloxy group substituted with a water-soluble substituent into each benzene ring of a fat-soluble dye.

1. A luminescent compound having a structure represented by a general formula (1) below,

[Chem. 1]

General formula (1)

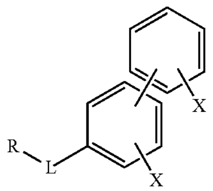

wherein R represents a luminescent dye skeleton, X represents an ionic substituent, and L represents a single bond, an oxygen atom, a sulfur atom, a selenium atom or an NH group.

2. The luminescent compound according to item 1, wherein the structure represented by the general formula (1) has a structure represented by a general formula (2) below,

[Chem. 2]

General formula (2)

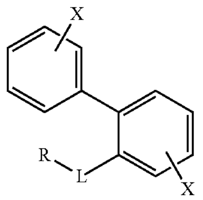

wherein R represents a luminescent dye skeleton, X represents an ionic substituent, and L represents a single bond, an oxygen atom, a sulfur atom, a selenium atom or an NH group.

3. The luminescent compound according to item 1 or 2, in which, in the general formula (1), the luminescent dye skeleton represented by R has a structure represented by any one of cores shown below,

[Chem. 3]

R=

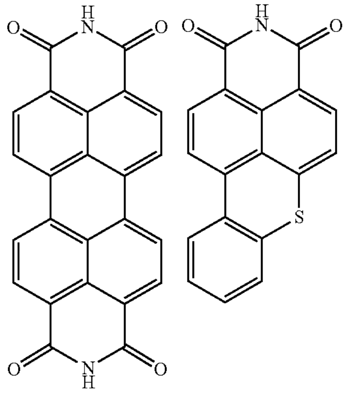

-continued

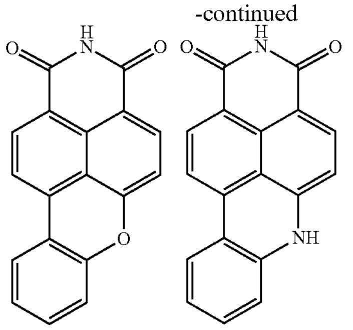

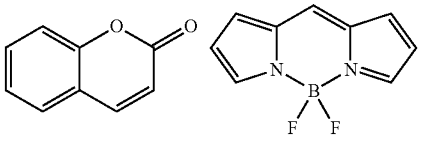

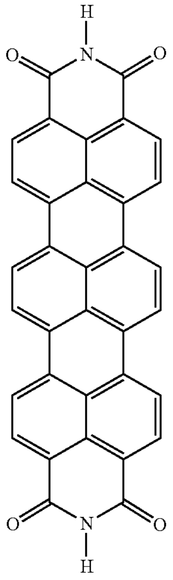

4. The luminescent compound according to any one of items 1 to 3, wherein, in the general formula (1), the ionic substituent represented by X is any one of a sulfo group, a phosphoric acid group, a sulfonic acid ester group, a phosphoric acid ester group, an ammonium group, or a salt thereof.

5. The luminescent compound according to any one of items 1 to 4, wherein, in the general formula (1), L is an oxygen atom.

6. The luminescent compound according to any one of items 1 to 5, wherein, in the general formula (1), the ionic substituent represented by X is any one of a sulfo group and a salt thereof.

7. The luminescent compound according to any one of items 1 to 6, having a structure represented by general formula (3) below,

[Chem. 4]

General formula (3)

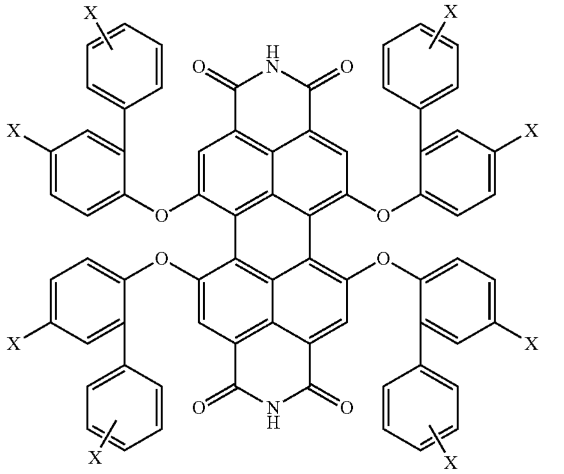

wherein X represents a sulfo group or a salt thereof.

8. A method for producing a luminescent compound, in which the luminescent compound according to any one of items 1 to 7 is produced, including:

introducing one sulfo group into each benzene ring by sulfonation of a dye molecule having a 2-biphenyloxy group,

[Chem. 5]

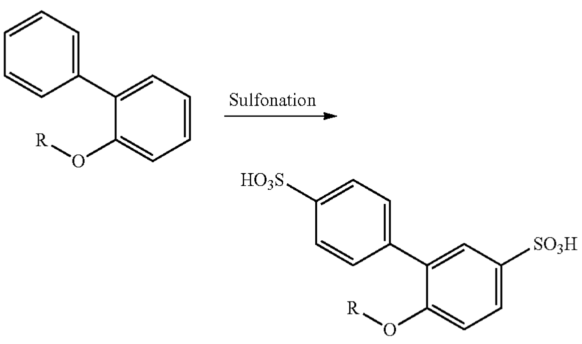

wherein R represents a luminescent dye skeleton.

9. A luminescent composition including: the luminescent compound according to any one of items 1 to 7.

10. A luminescent thin film, including: the luminescent compound according to any one of items 1 to 7.

11. A luminescent particle containing the luminescent compound according to any one of items 1 to 7.

By the means of one or more embodiments of the present invention, it is possible to provide a luminescent compound having high water solubility and excellent luminescent properties due to a concentration quenching suppressing effect even under a high concentration condition and a method for producing the same, and it is also possible to provide a luminescent composition, a luminescent thin film, and a luminescent particle containing the luminescent compound.

In the luminescent compound of one or more embodiments of the present invention, a biphenyloxy group substituted with an ionic substituent which is a water-soluble substituent is introduced into each benzene ring of a fat-soluble dye. The interaction between the fat-soluble dye cores is suppressed by the electrostatic repulsion by the ionic substituents, and the aggregation between the molecules can be suppressed. As a result, it is assumed that quenching due to aggregation under high concentration conditions becomes smaller, and the luminescence property is improved.

BRIEF DESCRIPTION OF THE DRAWINGS

FIG. 1 shows changes in quantum yield of Compound 1-1 according to one or more embodiments of the present invention, Comparative Compound 1, and Comparative Compound 2 when dye doping concentration is increased.

DETAILED DESCRIPTION

The luminescent compound of one or more embodiments of the present invention has a structure represented by the aforementioned general formula (1).

This feature is a technical feature common to or corresponding to each of the following embodiments.

In one or more embodiments of the present invention, the structure represented by the general formula (1) may have a structure represented by the general formula (2) in terms of excellent concentration quenching suppressing effect.

In the general formula (1), the luminescent dye skeleton represented by R may have a structure represented by any one of the cores shown above from the viewpoint of excellent concentration quenching suppressing effect.

In the general formula (1), the ionic substituent represented by X may be any one of a sulfo group, a phosphoric acid group, a sulfonic acid ester group, a phosphoric acid ester group, an ammonium group, or a salt thereof from the viewpoint of excellent concentration quenching suppressing effect.

In addition, in the general formula (1), L may be an oxygen atom and the ionic substituent represented by X may be either a sulfo group or a salt thereof from the viewpoint of excellent concentration quenching suppressing effect.

Furthermore, the luminescent compound having the structure represented by the aforementioned general formula (1) may have the structure represented by the aforementioned general formula (3) in terms of excellent concentration quenching suppressing effect.

In the method for producing the luminescent compound according to one or more embodiments of the present invention, one sulfo group is introduced into each benzene ring by sulfonation of a dye molecule having a 2-biphenyloxy group(s). Thus, substitution with a plurality of ionic substituents can be performed at a time, leading to excellent production efficiency.

The luminescent compound according to one or more embodiments of the present invention is suitably used for a luminescent composition, a luminescent thin film, and a luminescent particle.

Hereinafter, the present invention, constituent elements thereof, and embodiments and modes for carrying out the present invention will be described. In the present description, "to" is used to indicate that figures before and after "to" are included as a lower limit value and an upper limit value.

[Luminescent Compound]

The luminescent compound according to one or more embodiments of the present invention has a structure represented by the following general formula (1).

[Chem. 6]

General formula (1)

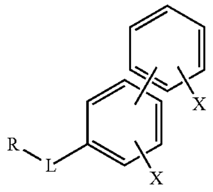

[In the formula, R represents a luminescent dye skeleton. X represents an ionic substituent. L represents a single bond, an oxygen atom, a sulfur atom, a selenium atom or an NH group.]

In the general formula (1), the luminescent dye skeleton represented by R may have a structure represented by any one of the following cores.

[Chem. 7]

R=

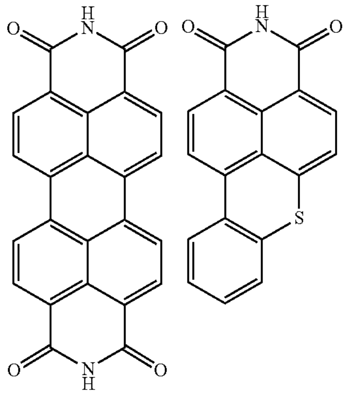

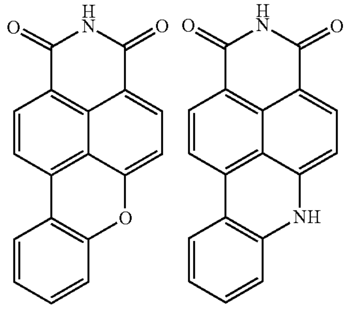

-continued

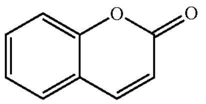

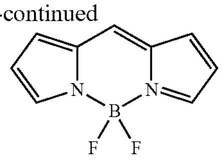

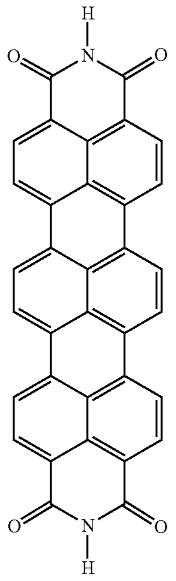

In the general formula (1), the ionic substituent represented by X may be any one of a sulfo group, a phosphoric acid group, a sulfonic acid ester group, a phosphoric acid ester group, an ammonium group, a carboxy group, a phosphonium group, or a salt thereof. Among these, a sulfo group, a phosphoric acid group, a sulfonic acid ester group, a phosphoric acid ester group, an ammonium group, or a salt thereof may be more preferable, and a sulfo group or a salt thereof may be particularly preferable. Specific examples of the ionic substituents include $—SO_3H$, $—SO_3Na$, $—OSO_3H$, $—OSO_3Na$, $—SO_3NH_4$, $—PO_4H_2$, $—PO_4Na$, $—OPO_3H_2$, $—OPO_3Na_2$, $—NMe_3OH$, and $—NMe_3Cl$.

In the general formula (1) described above, L represents a single bond, an oxygen atom, a sulfur atom, a selenium atom or an NH group, and may be particularly preferably an oxygen atom.

In one or more embodiments, the structure represented by the general formula (1) may be a structure represented by the following general formula (2) in terms of excellent concentration quenching suppressing effect.

[Chem. 8]

General formula (2)

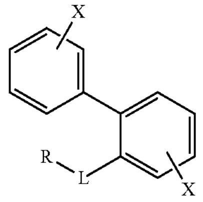

[In the formula, R represents a luminescent dye skeleton. X represents an ionic substituent. L represents a single bond, an oxygen atom, a sulfur atom, a selenium atom or an NH group.]

In the general formula (2), R, X and L have the same meanings as R, X and L in the general formula (1).

In addition, the luminescent compound according to one or more embodiments of the present invention may have a structure represented by the following general formula (3) from the viewpoint of excellent concentration quenching suppressing effect.

[Chem. 9]

General formula (3)

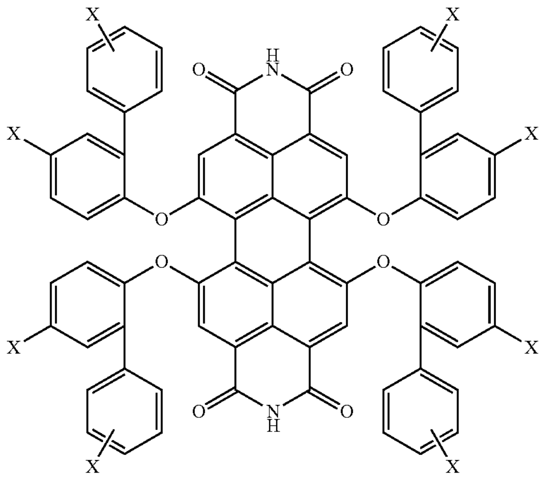

wherein X represents a sulfo group or a salt thereof.

Specific compounds of the luminescent compound having the structure represented by the above general formula (1) are shown below. However, the luminescent compound having the structure represented by the general formula (1) is not limited thereto.

[Chem. 10]
1-1
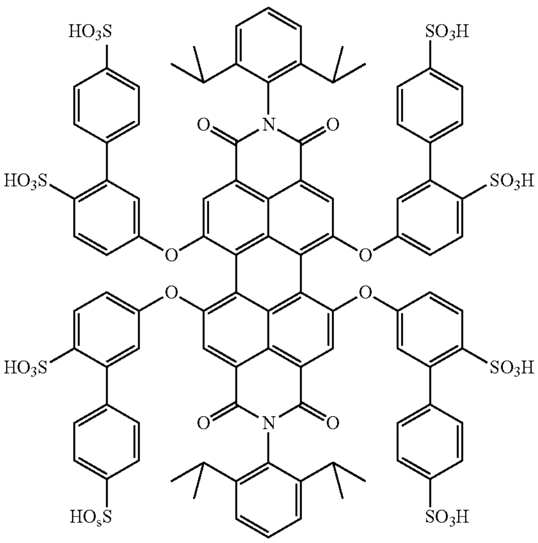
1-2
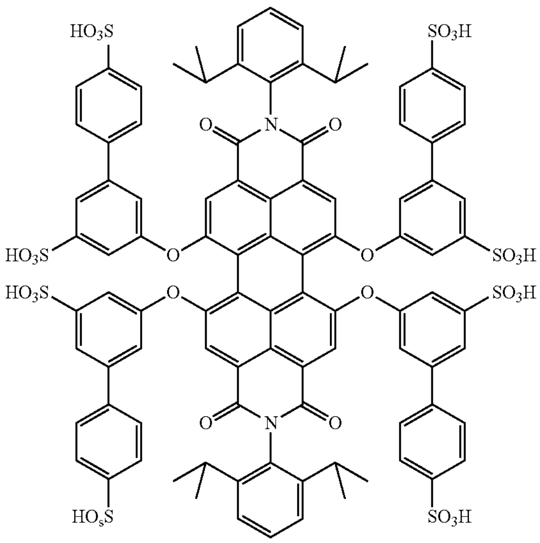
[Chem. 11]
1-3
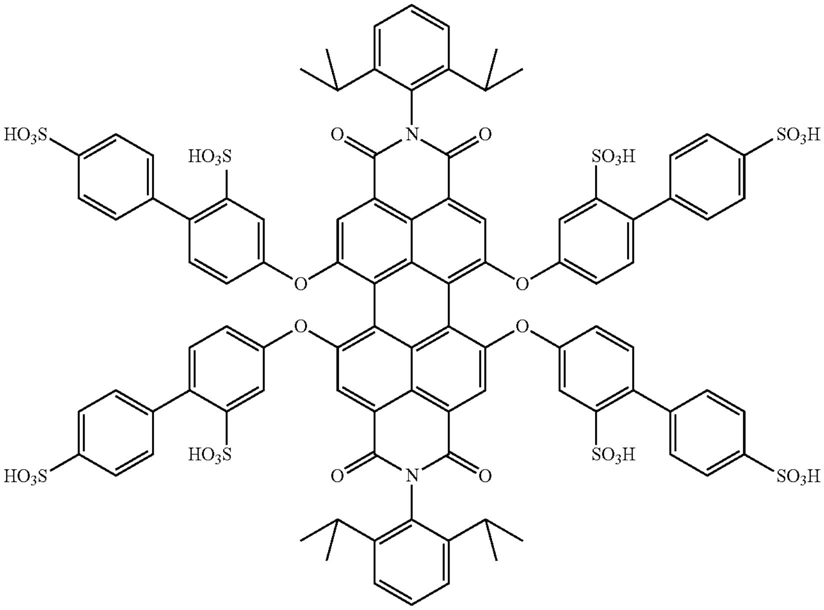

-continued
1-4
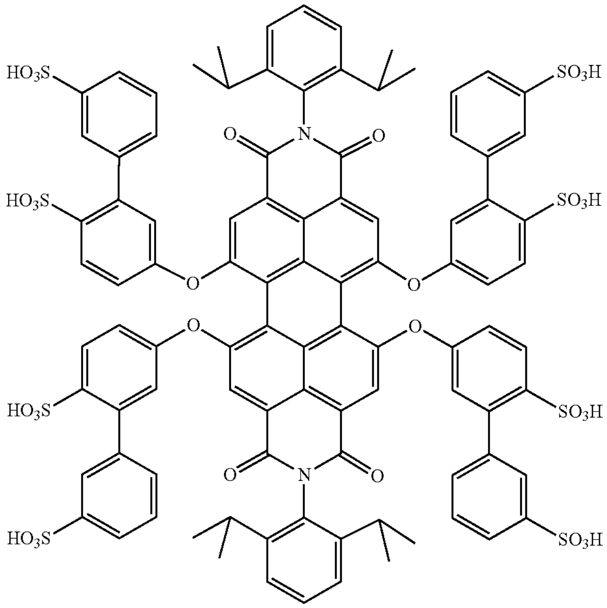
[Chem. 12]
1-5
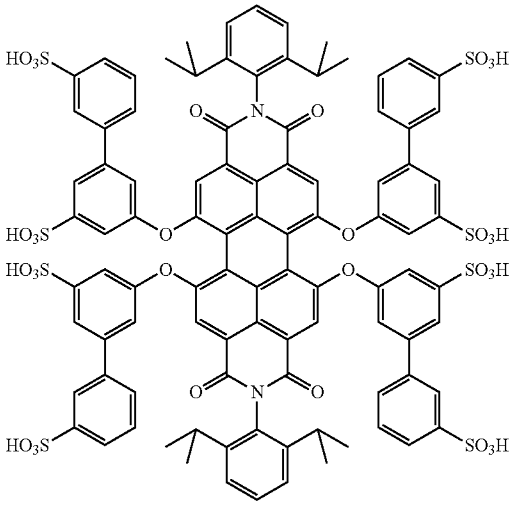
1-6
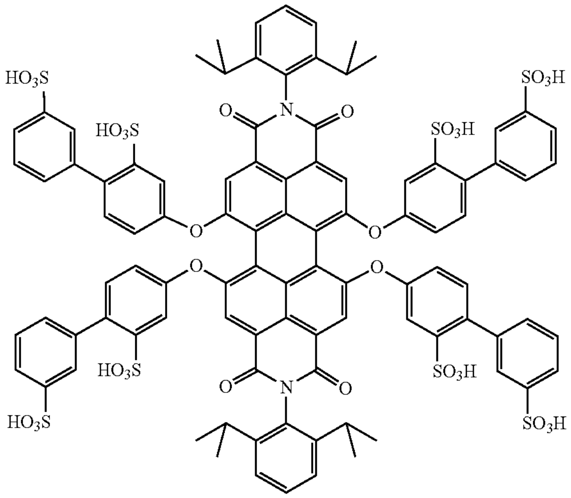

-continued
[Chem. 13]
2-1
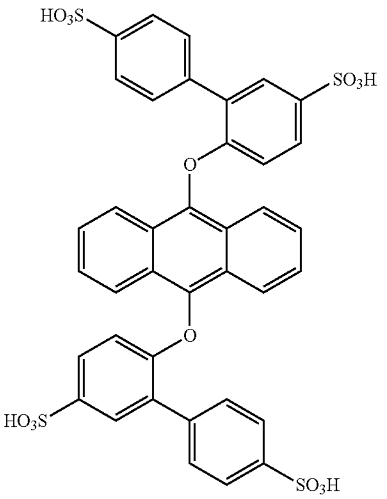
2-2
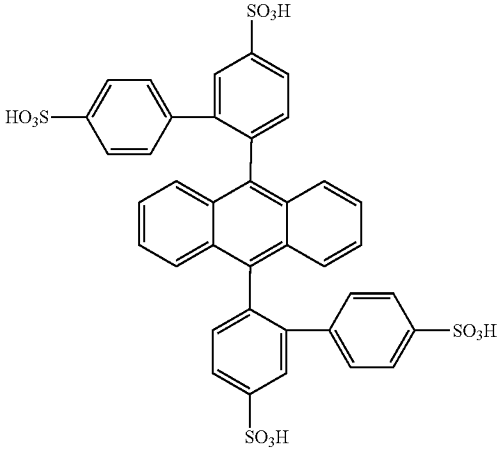
2-3
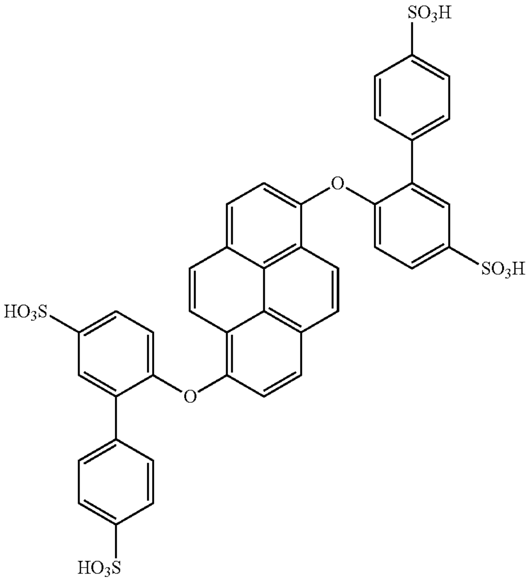
2-4
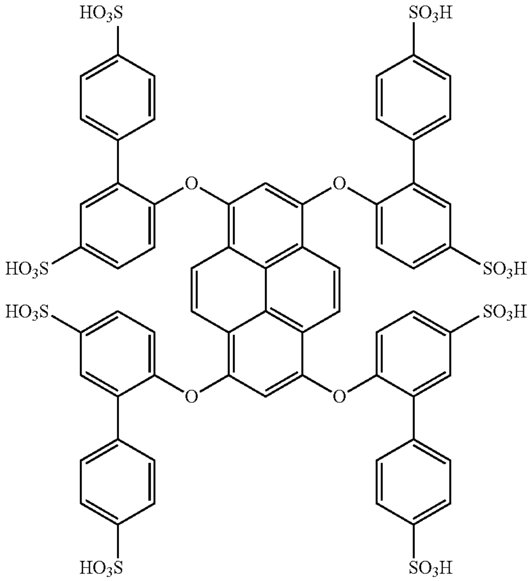
[Chem. 14]
2-5
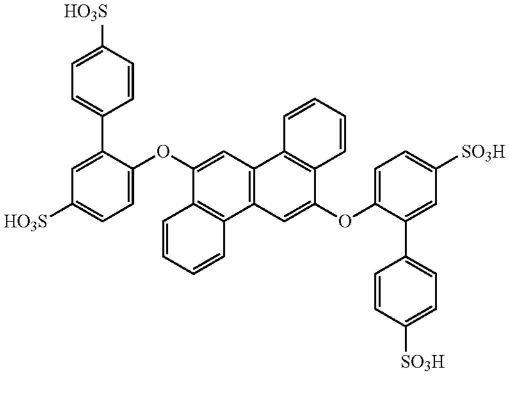
2-6
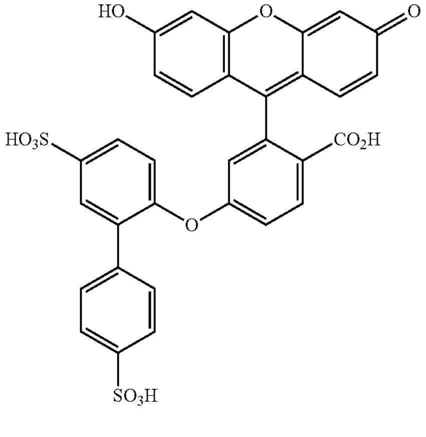

-continued
2-7
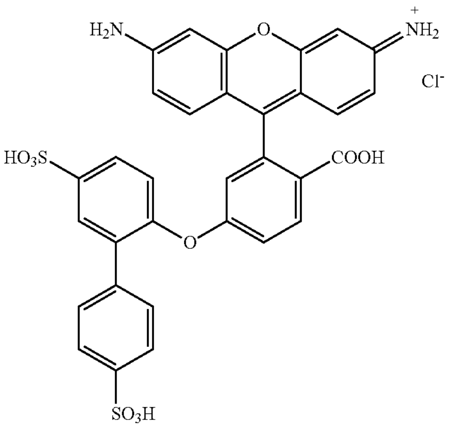
2-8
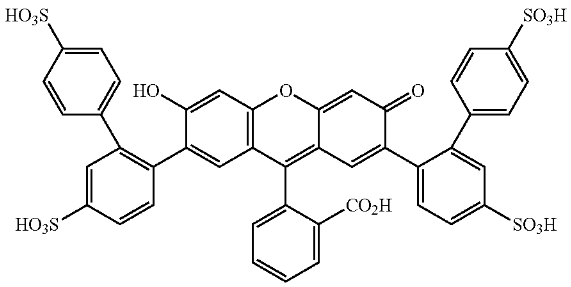
[Chem. 15]
2-9
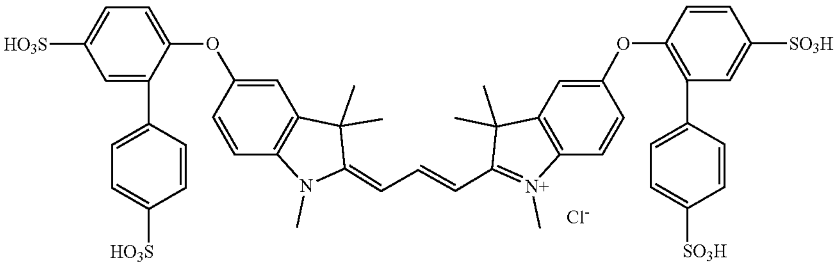
2-10
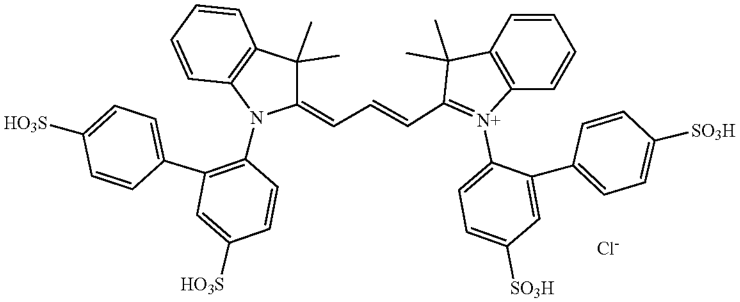

-continued
[Chem. 16]
3-1
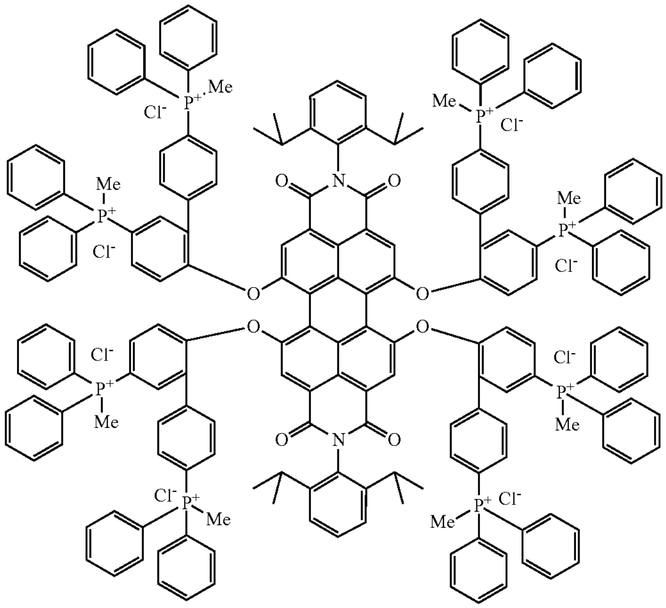
3-2
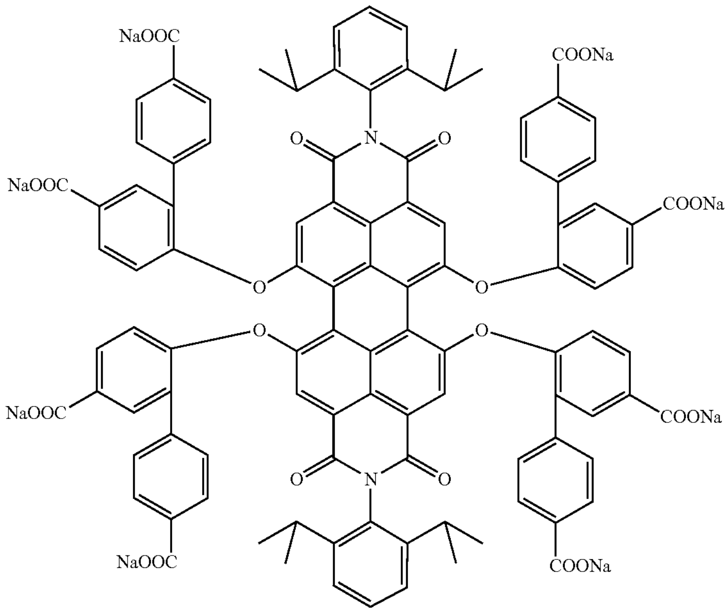

-continued
[Chem. 17]
3-3
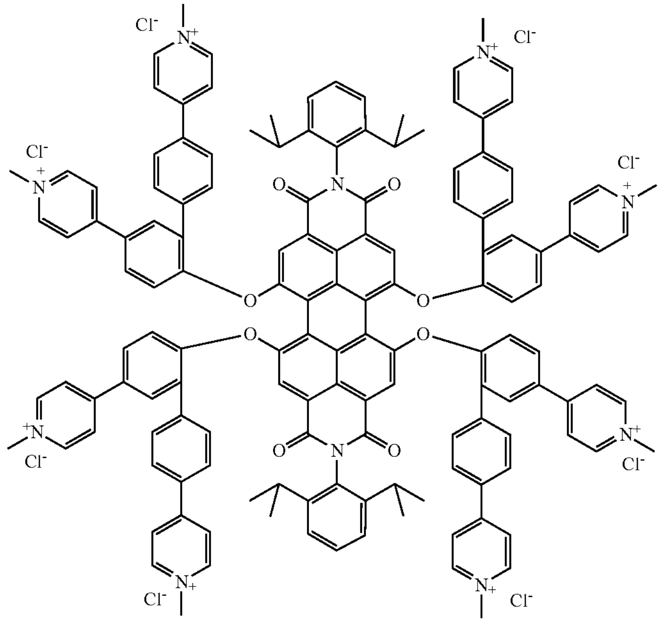
[Chem. 18]
4-1
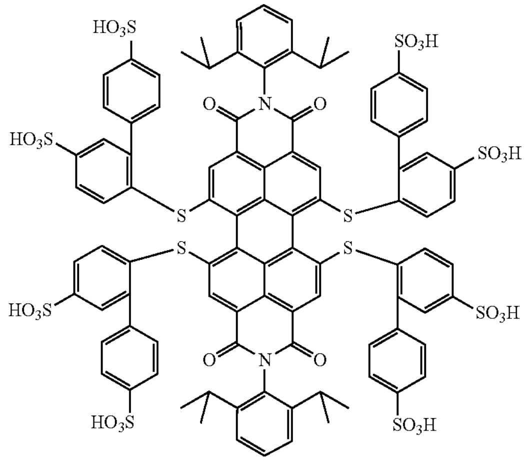
4-2
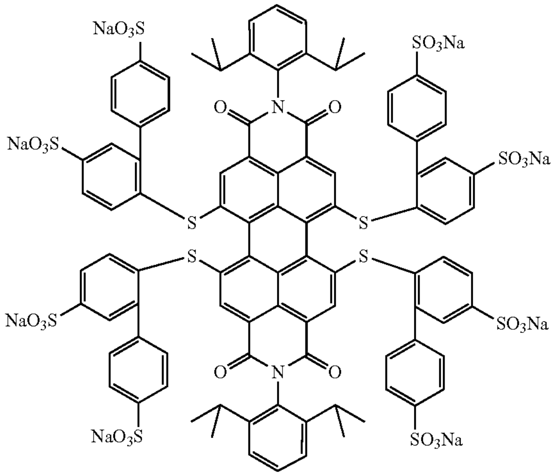

-continued
[Chem. 19]
4-3
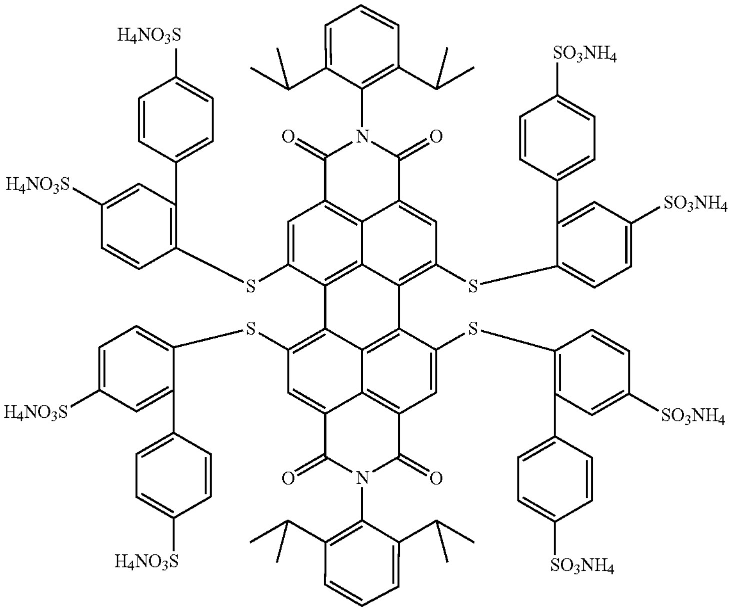
4-4
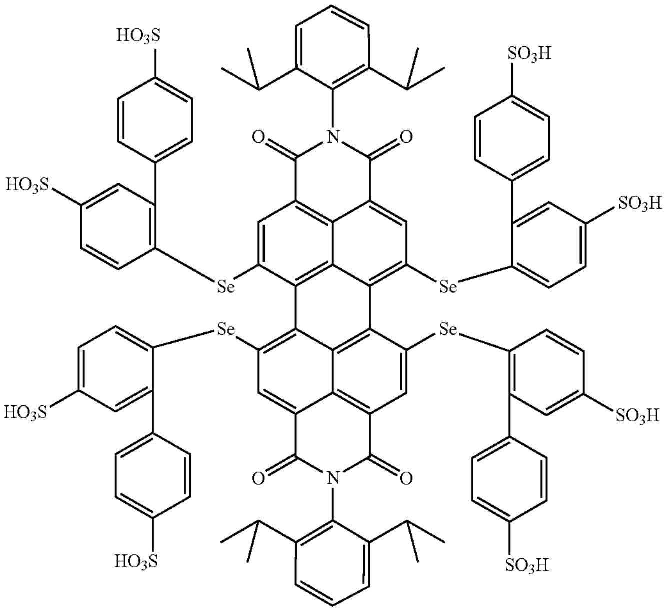

-continued
[Chem. 20]
4-5
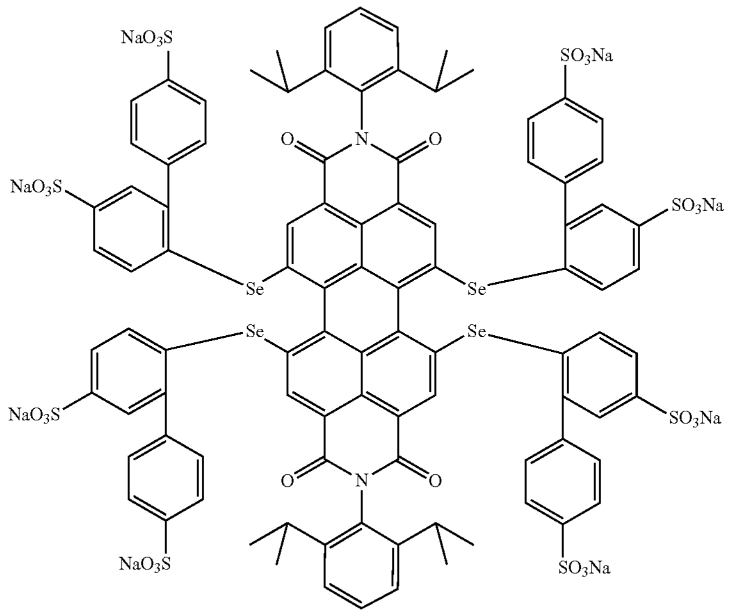
4-6
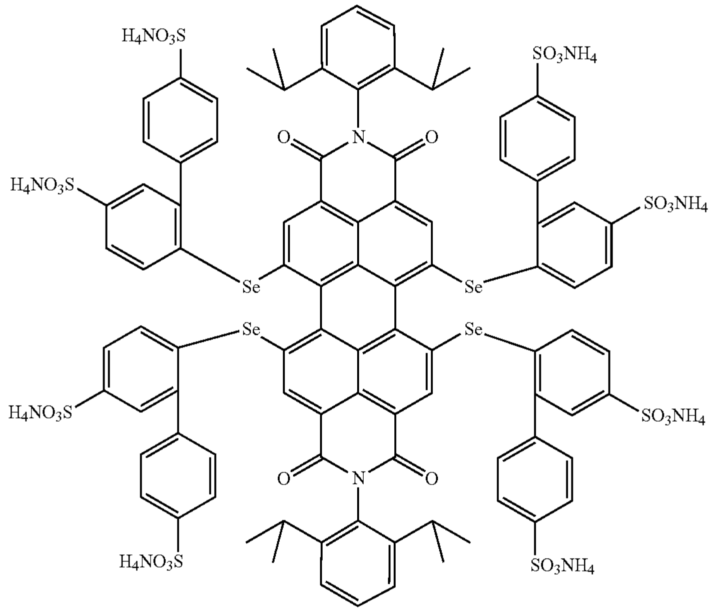

-continued
[Chem. 21]
4-7
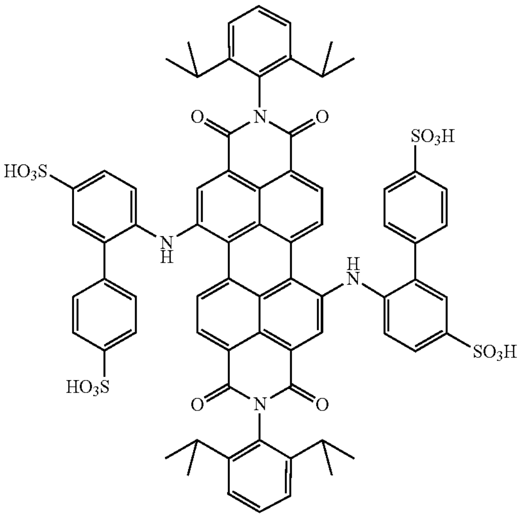
4-8
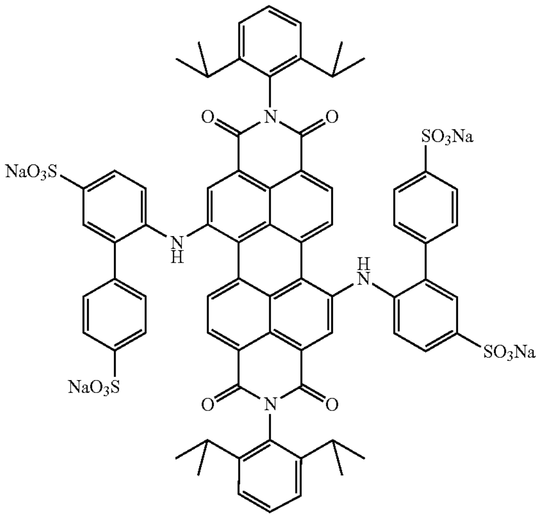
[Chem. 22]
4-9
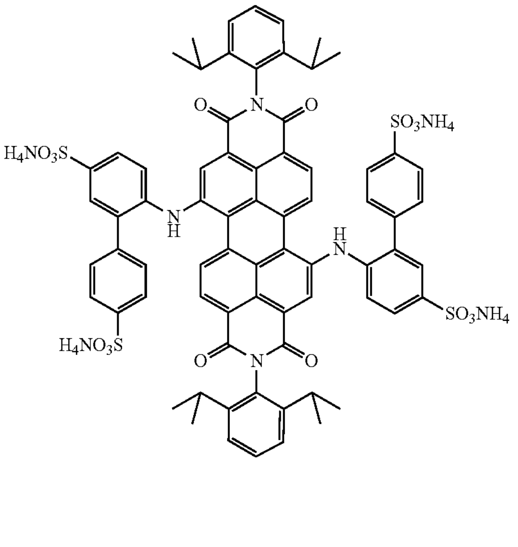
4-10
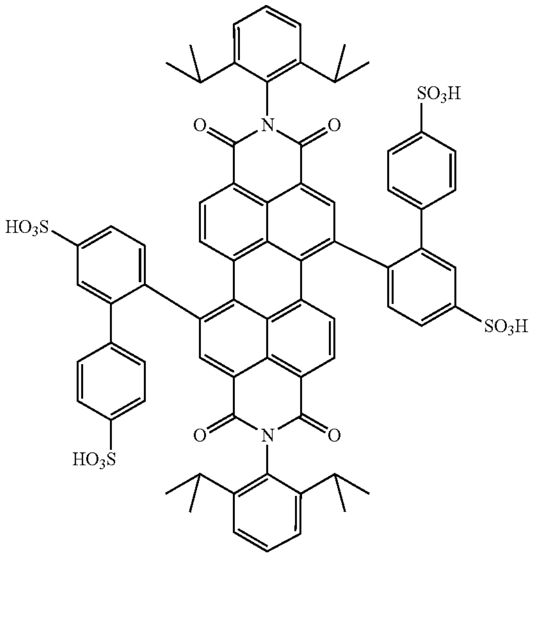

-continued
[Chem. 23]
4-11
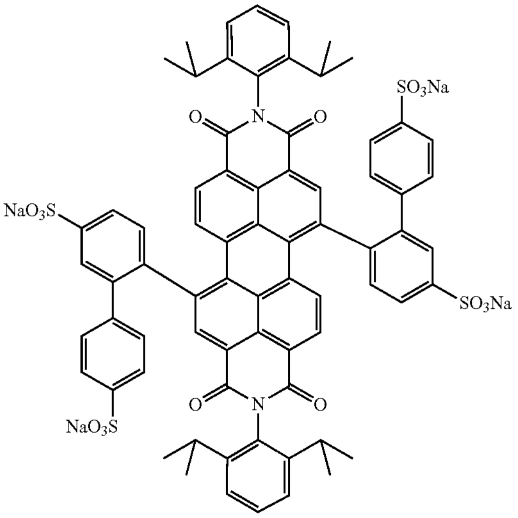
4-12
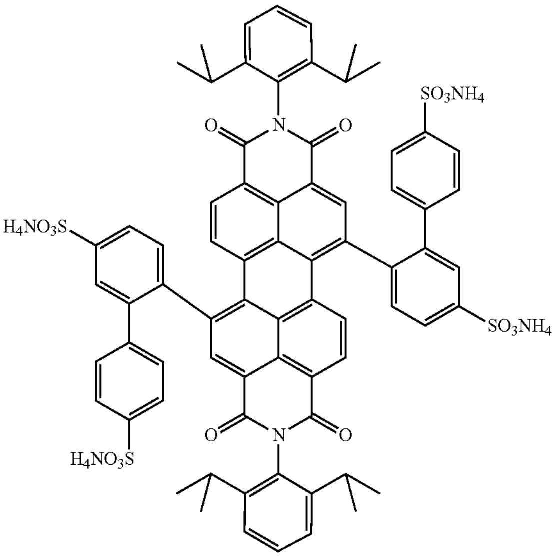
[Chem. 24]
5-1
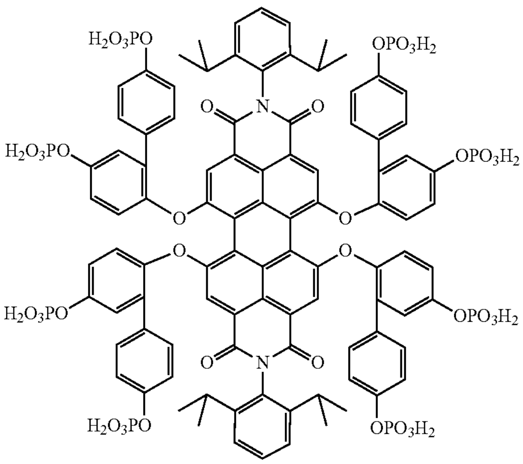
5-2
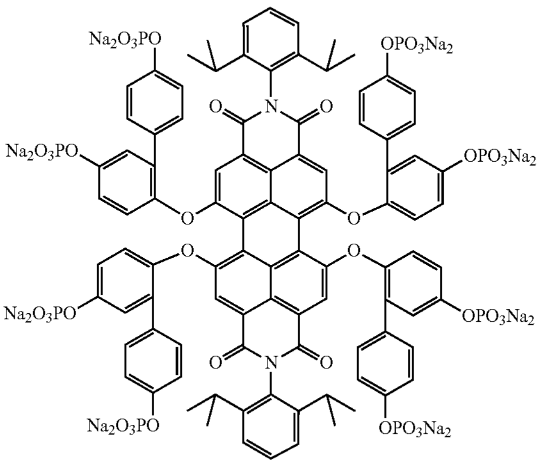
[Chem. 25]
5-3
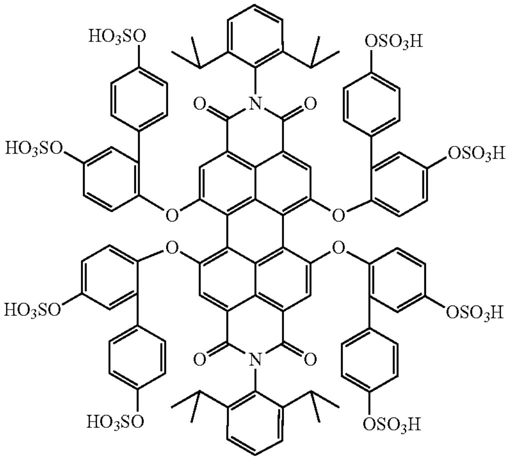
5-4
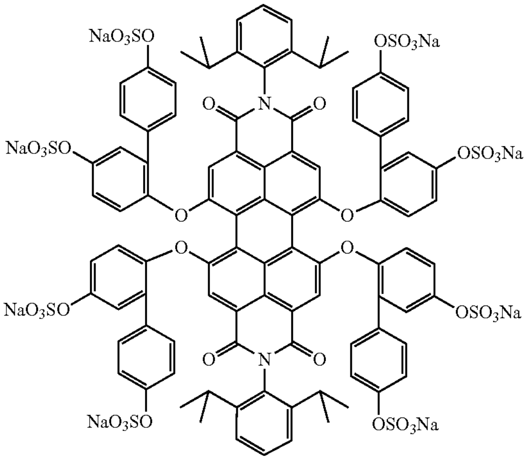

-continued
[Chem. 26]
5-5
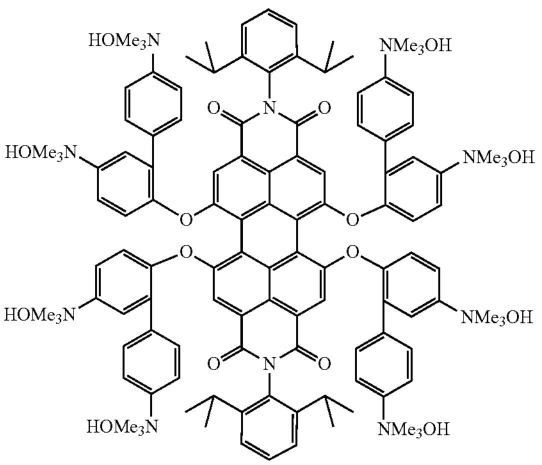
5-6
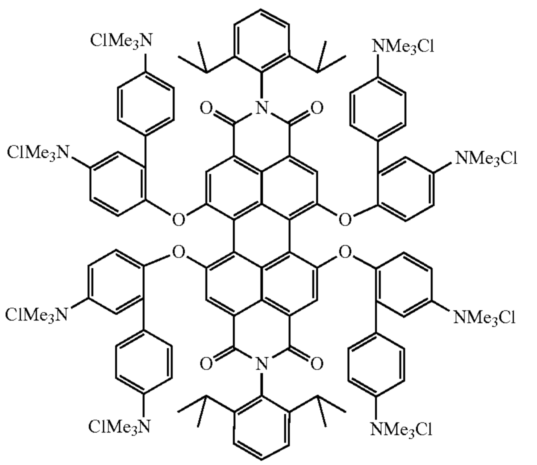
[Chem. 27]
6-1
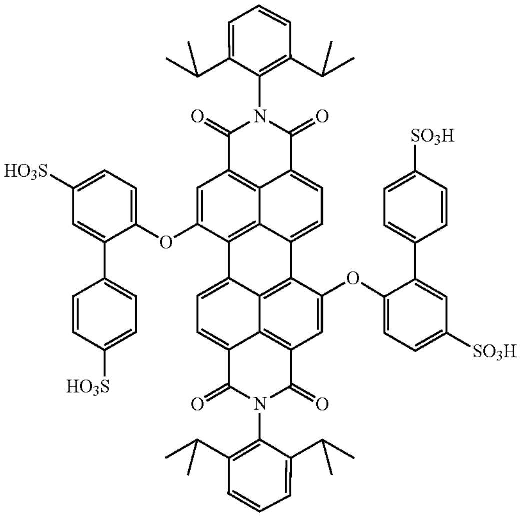
6-2
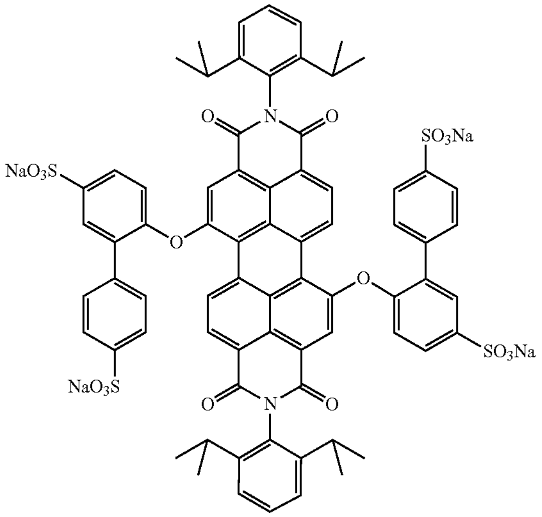
[Chem. 28]
6-3
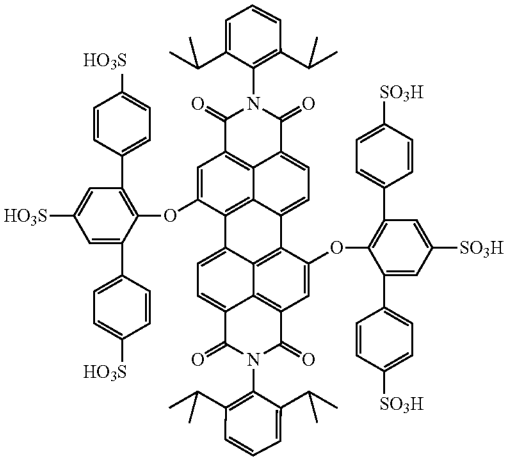
6-4
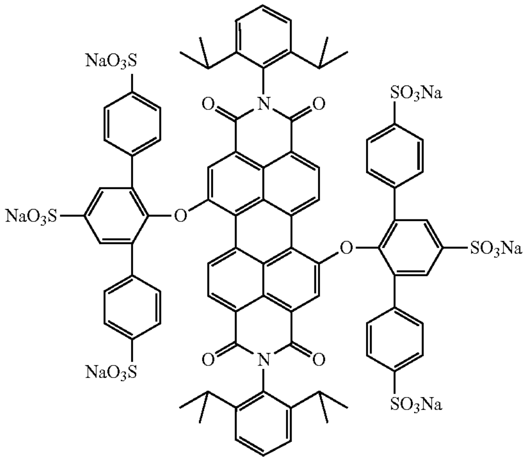

-continued
[Chem. 29]
6-5
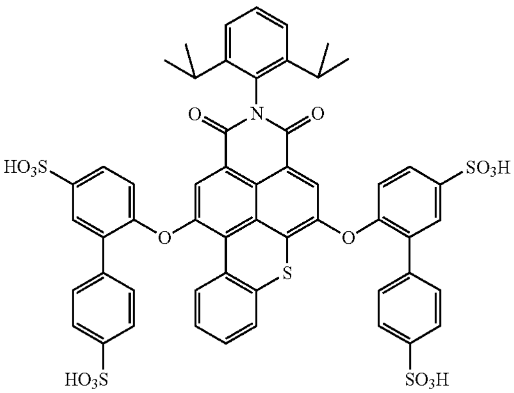
6-6
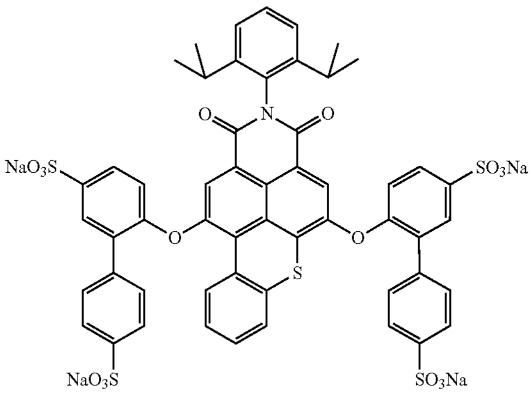
6-7
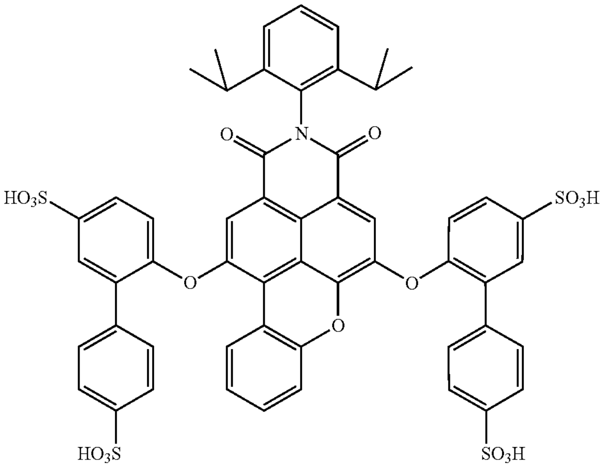
[Chem. 30]
6-8
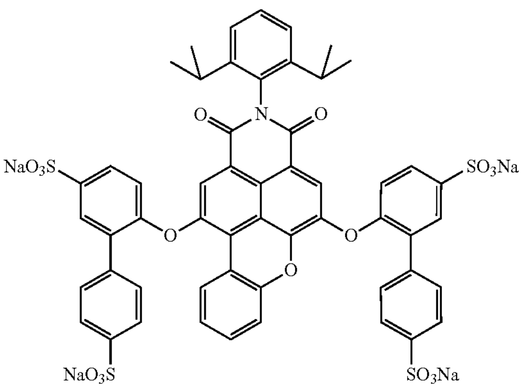
6-9
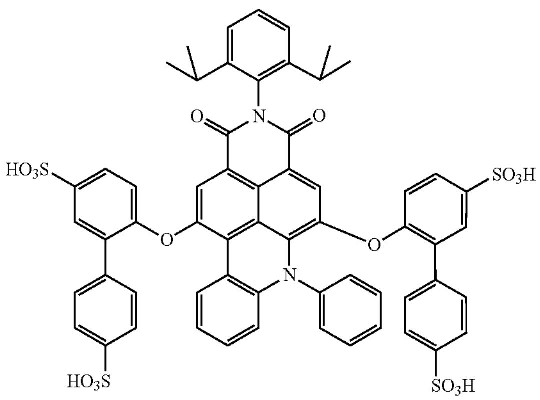

-continued
6-10
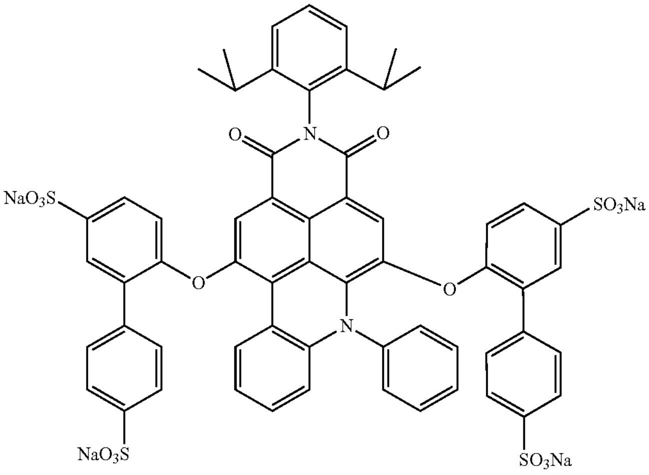
[Chem. 31]
6-11
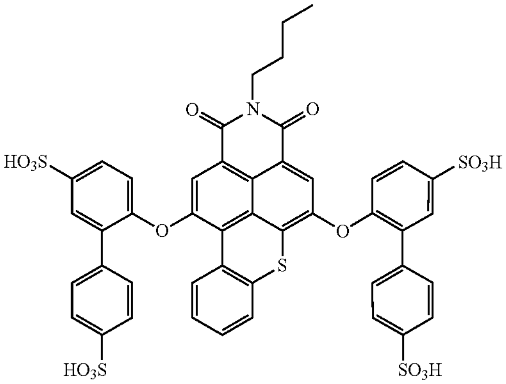
6-12
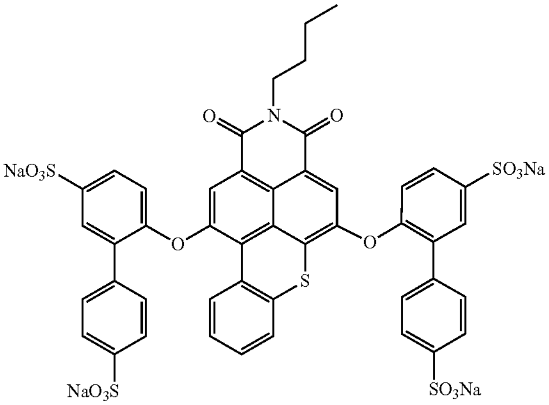
6-13
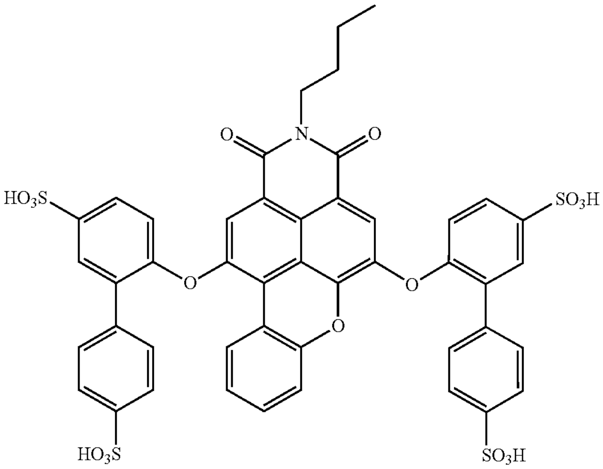

-continued
[Chem. 32]
6-14
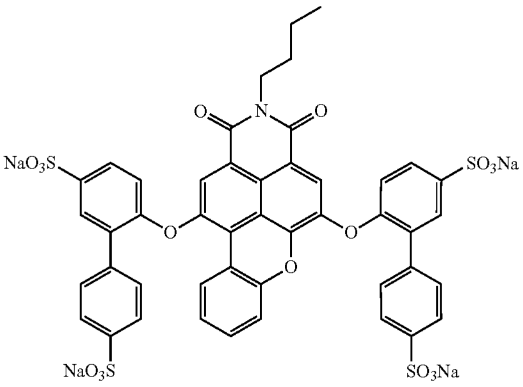
6-15
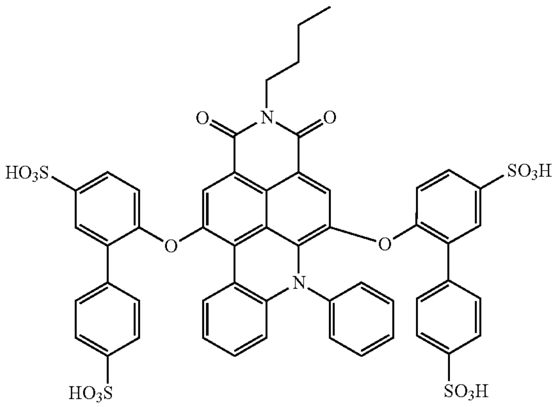
6-16
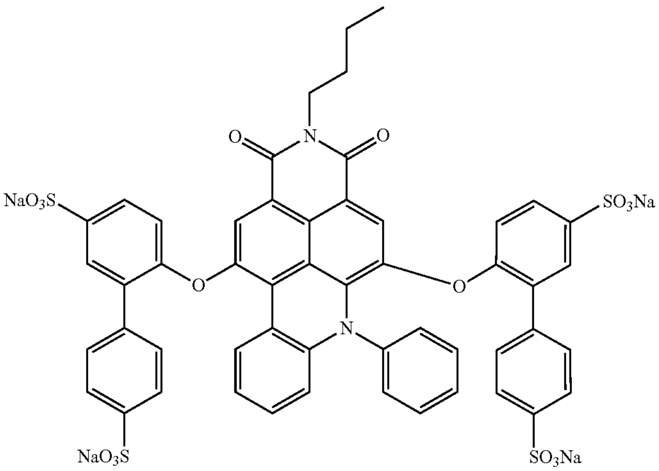
[Chem. 33]
6-17
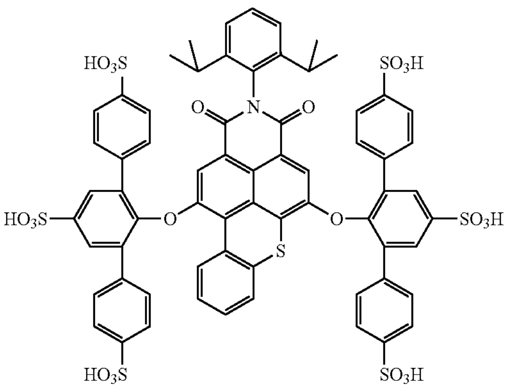
6-18
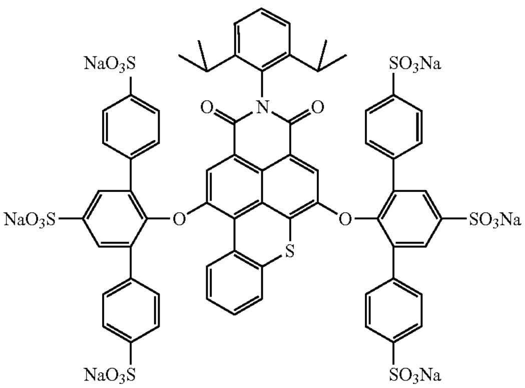

-continued
6-19
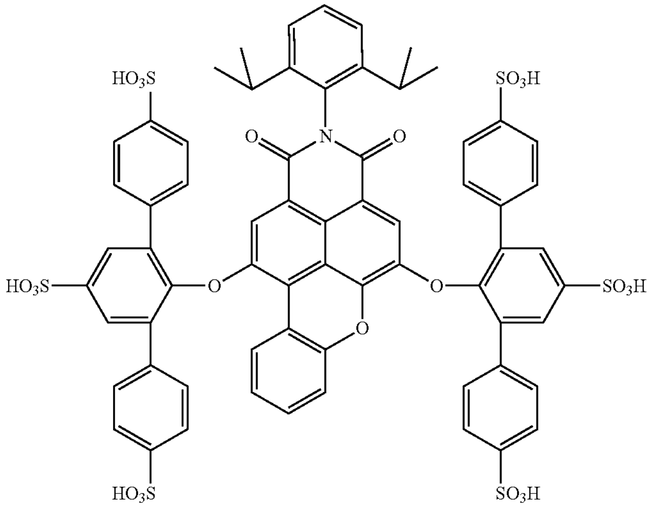
[Chem. 34]
6-20
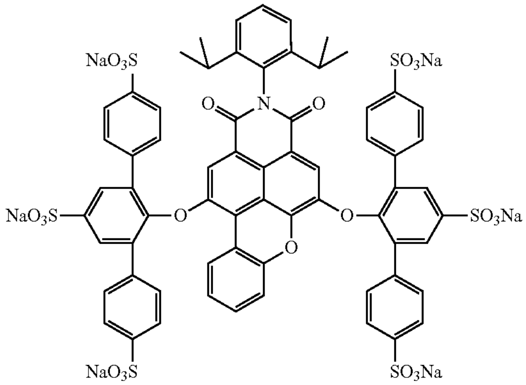
6-21
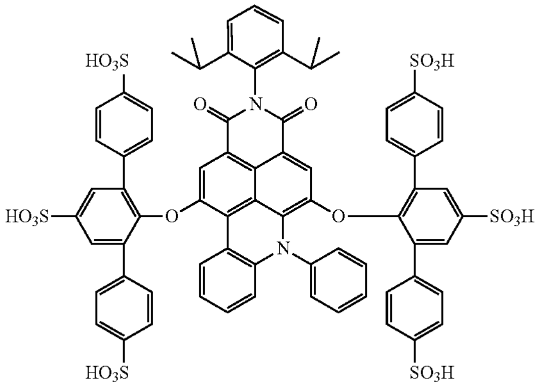
6-22
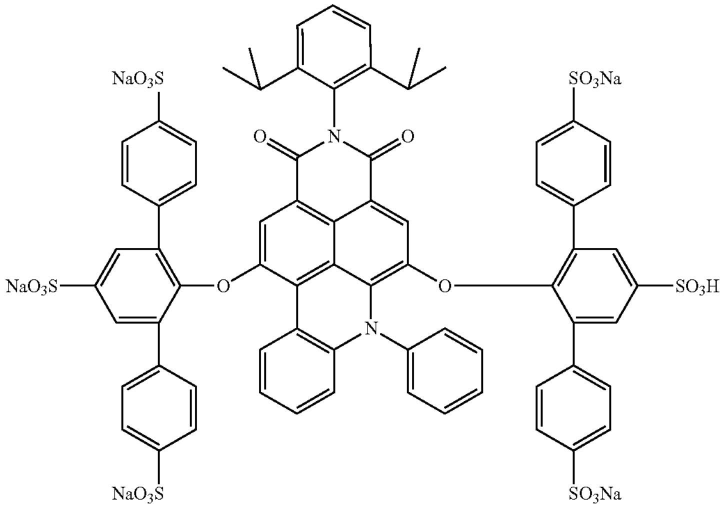

-continued
[Chem. 35]
6-23
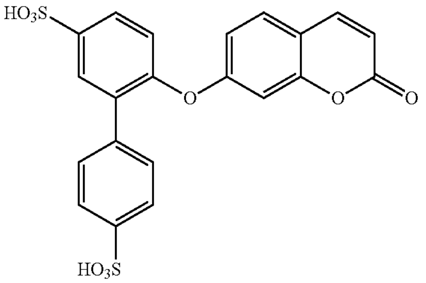
6-24
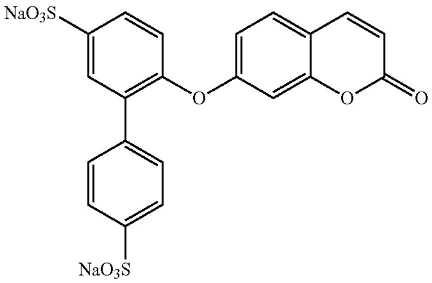
6-25
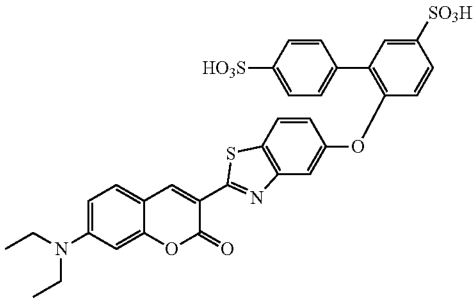
6-26
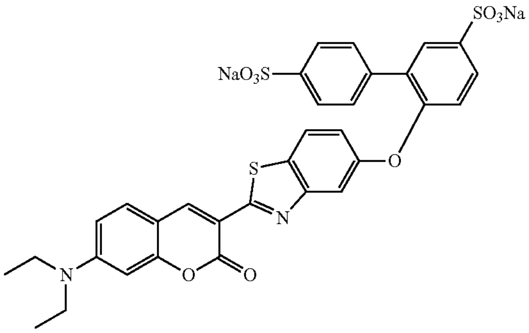
6-27
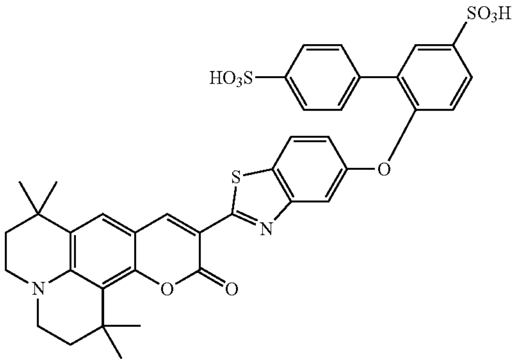
6-28
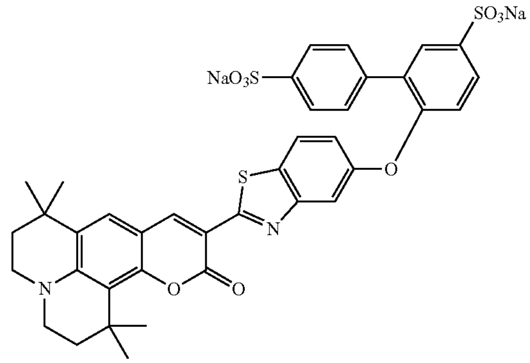
[Chem. 36]
6-29
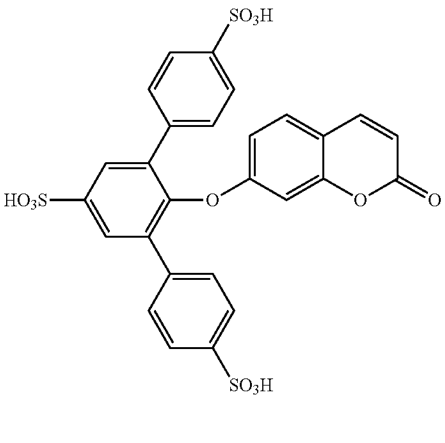
6-30
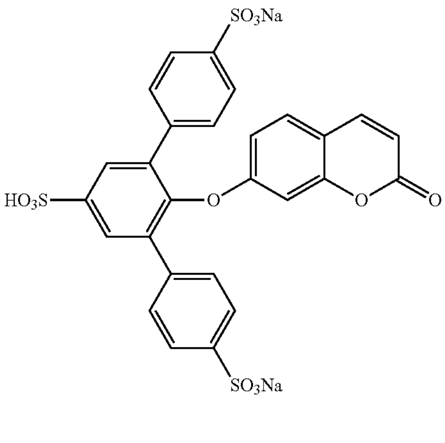

-continued
6-31
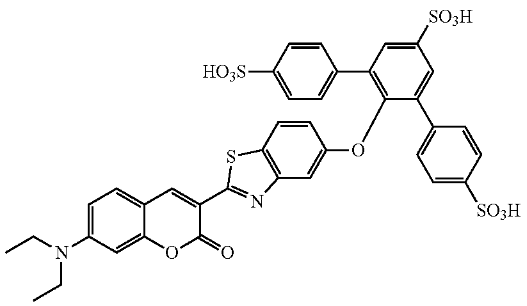
6-32
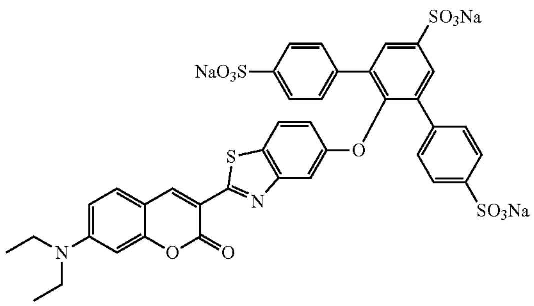
[Chem. 37]
6-33
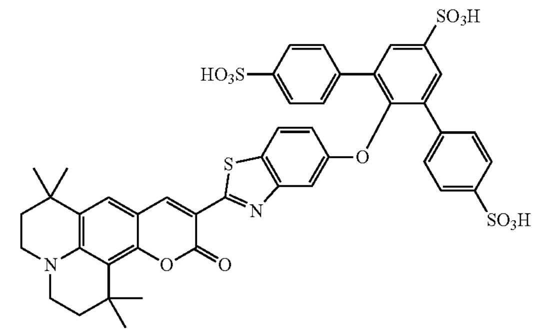
6-34
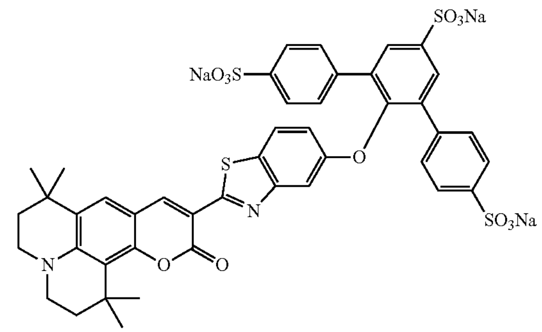
6-35
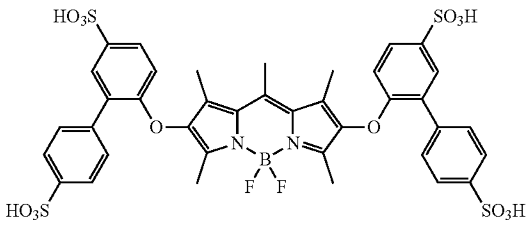
6-36
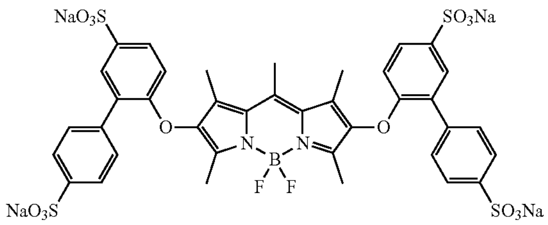
[Chem. 38]
6-37
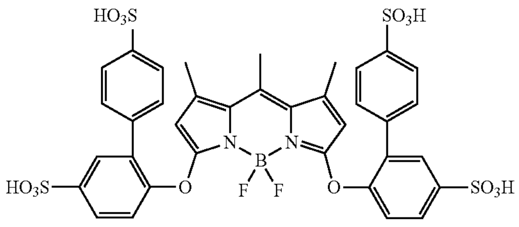
6-38
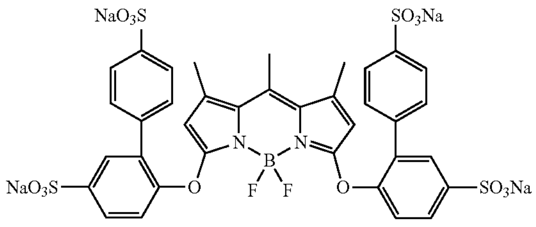
6-39
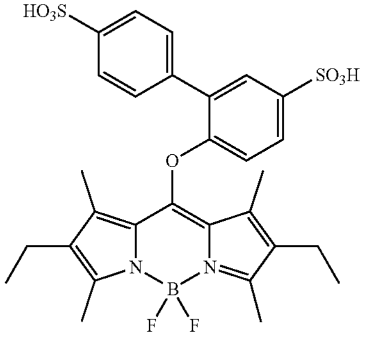
6-40
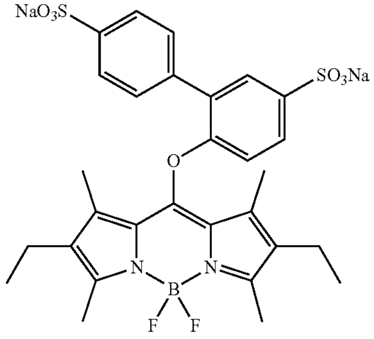

-continued
[Chem. 39]
6-41
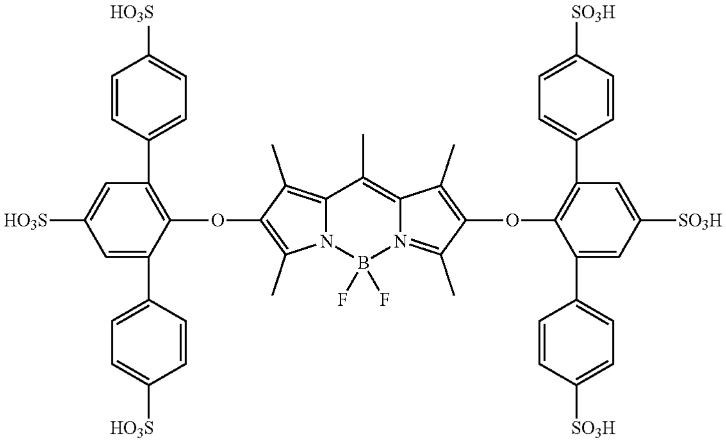
6-42
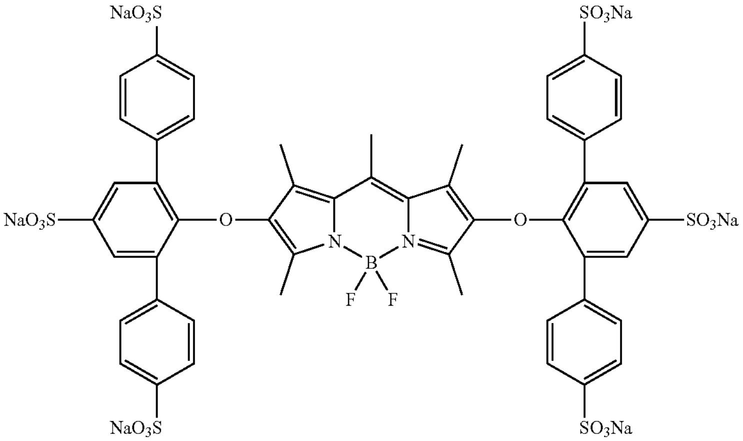
6-43
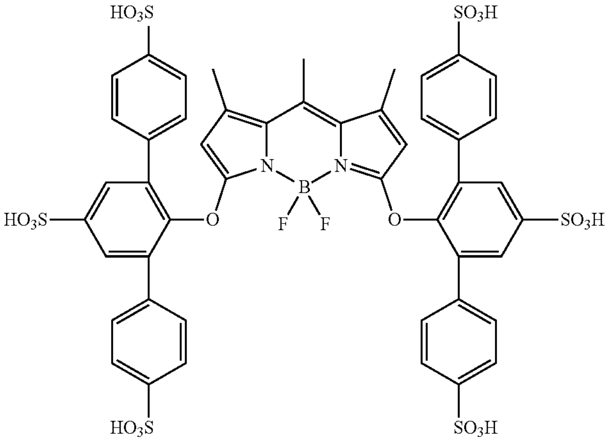

-continued
[Chem. 40]
6-44
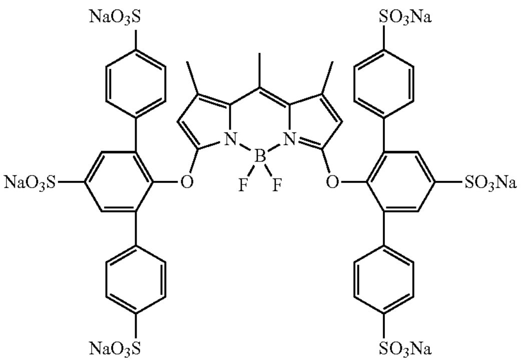
6-45
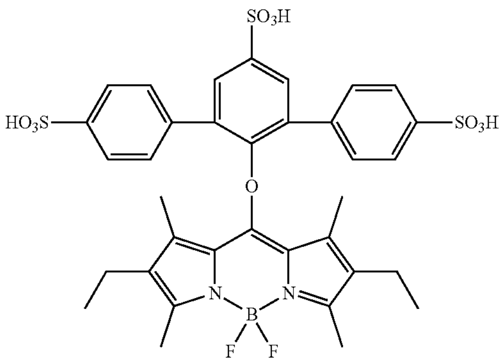
6-46
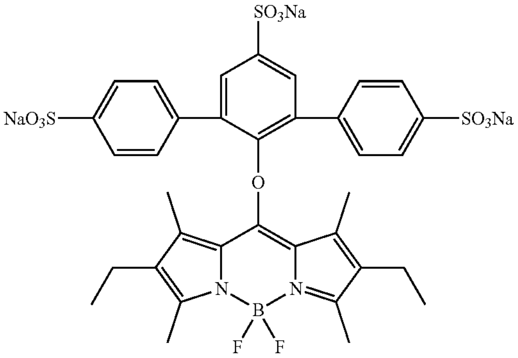
[Chem. 41]
7-1
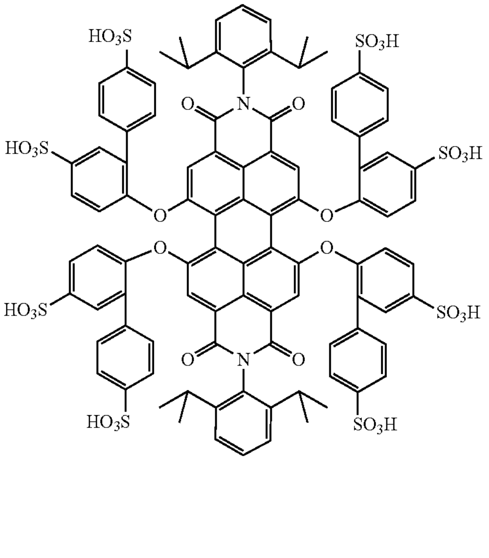
7-2
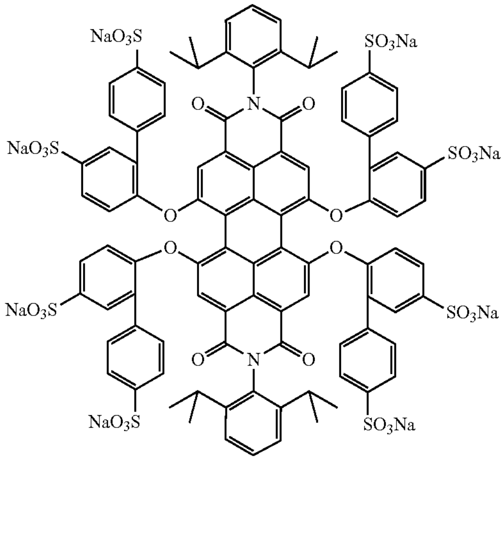

-continued
[Chem. 42]
7-3
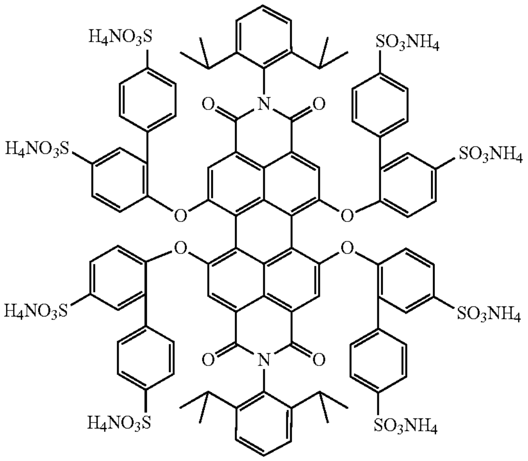
7-4
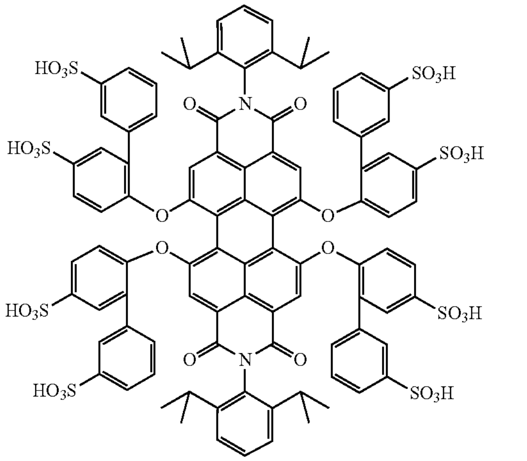
[Chem. 43]
7-5
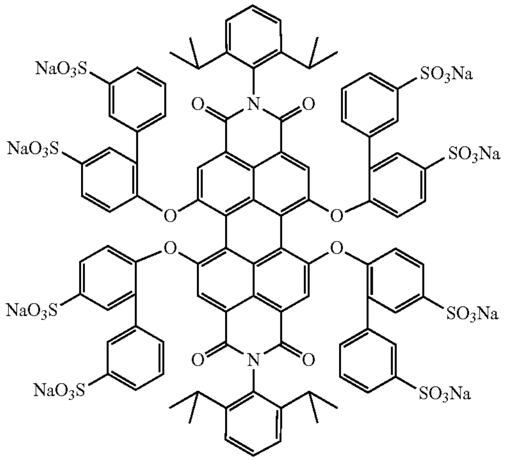
7-6
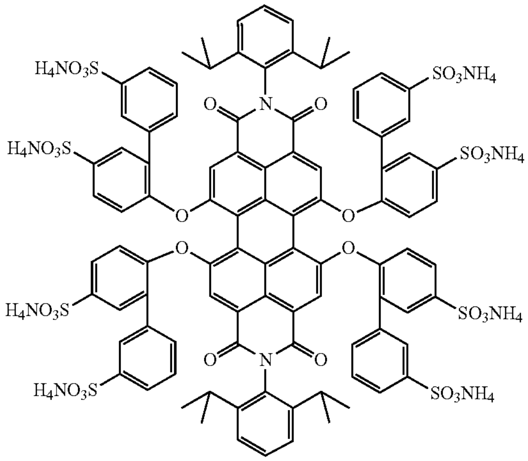
[Chem. 44]
7-7
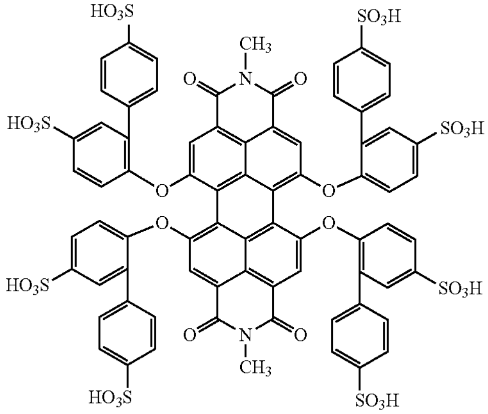
7-8
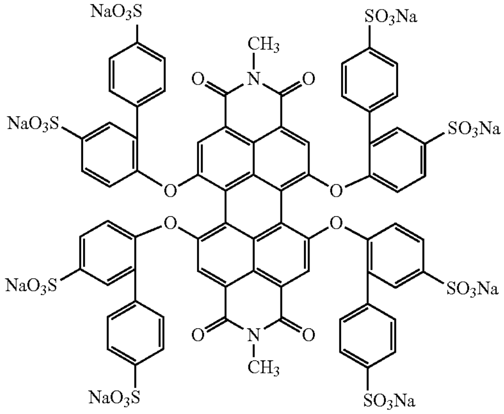

-continued
[Chem. 45]
7-9
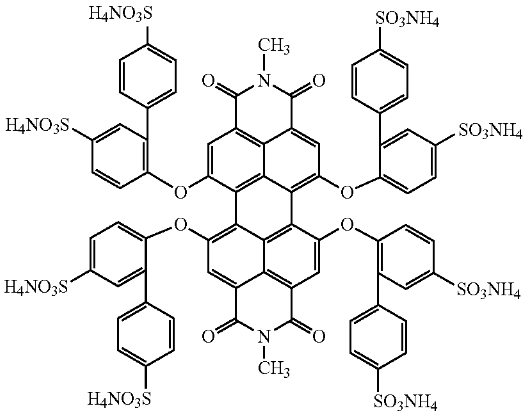
7-10
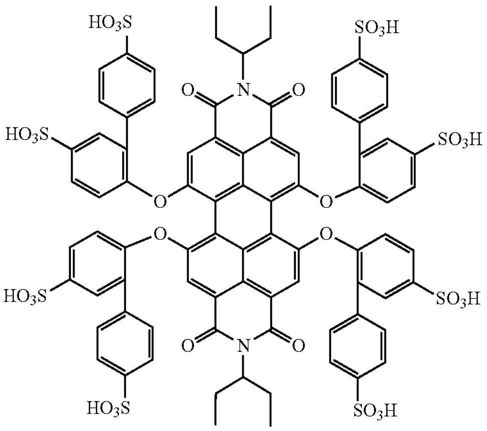
[Chem. 46]
7-11
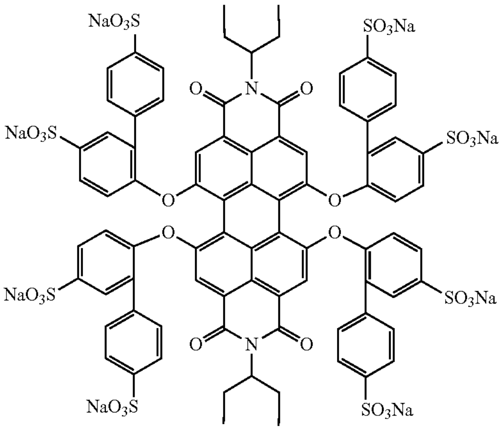
7-12
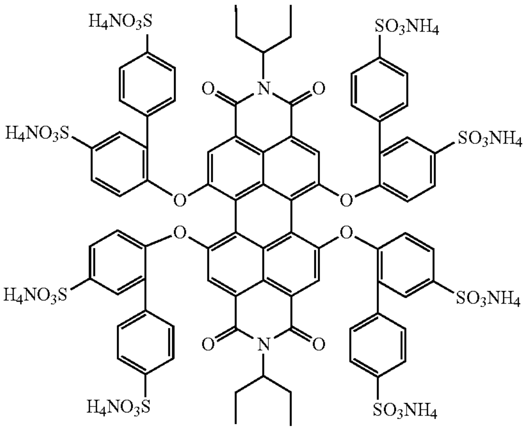
[Chem. 47]
7-13
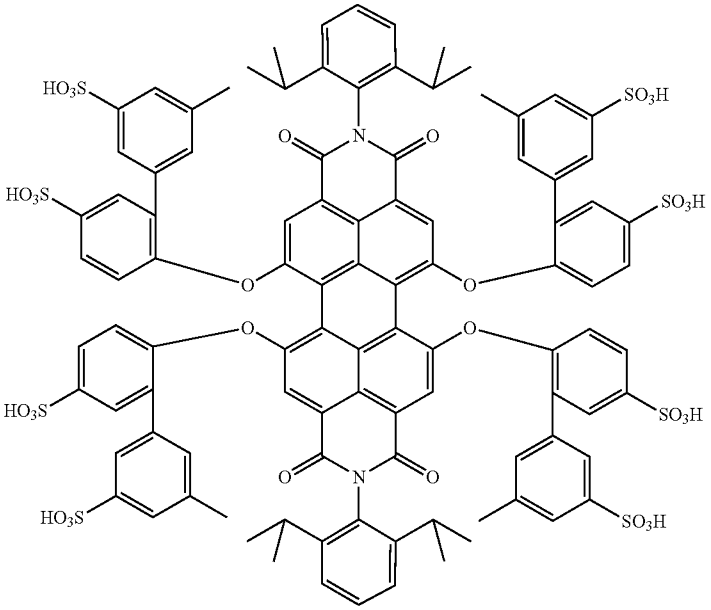

-continued
7-14
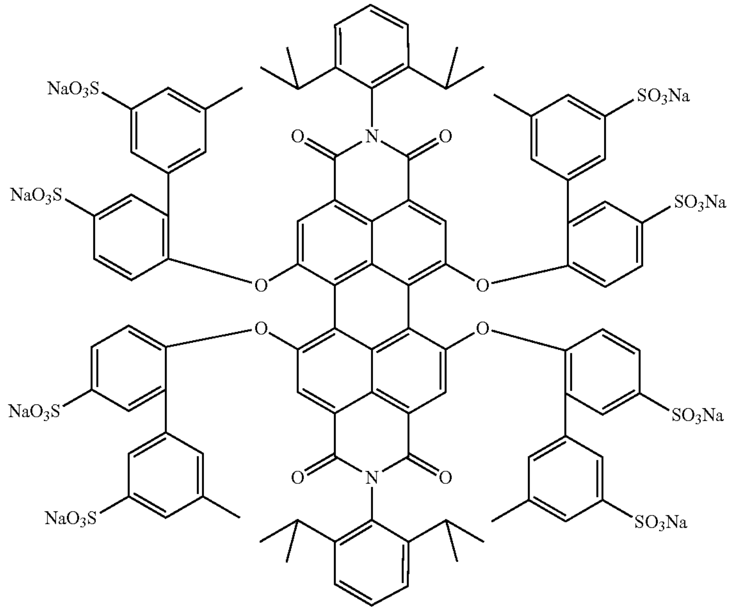
[Chem. 48]
7-15
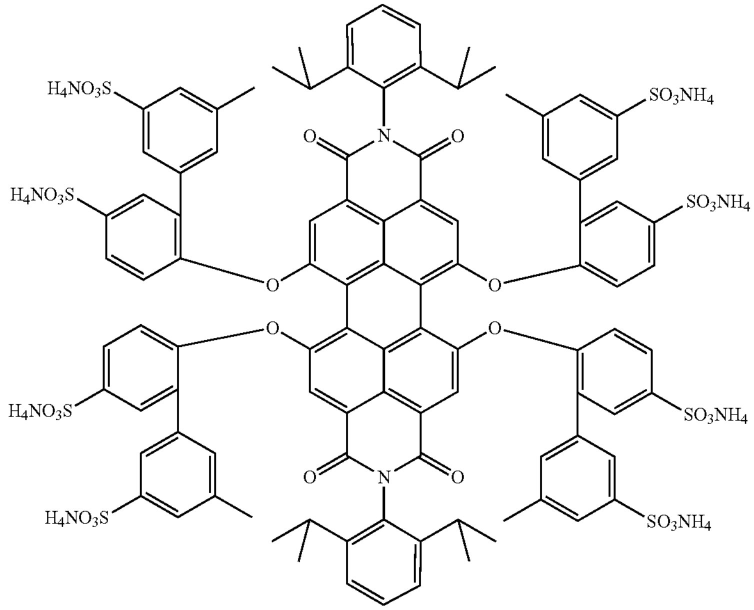

-continued
8-1
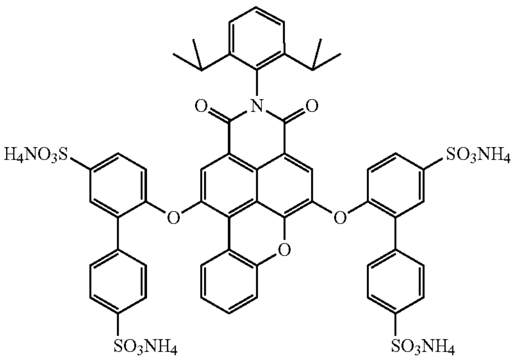
8-2
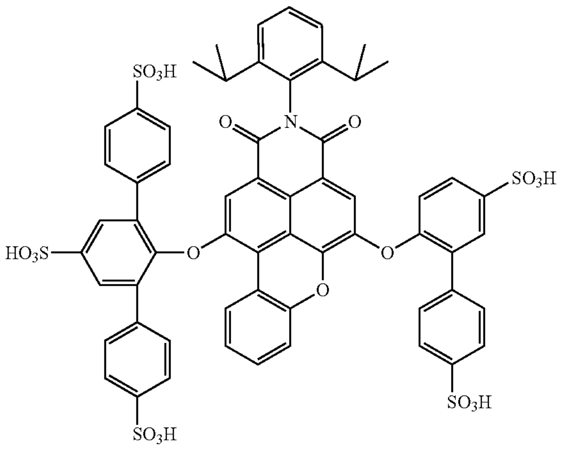
[Chem. 49]
8-3
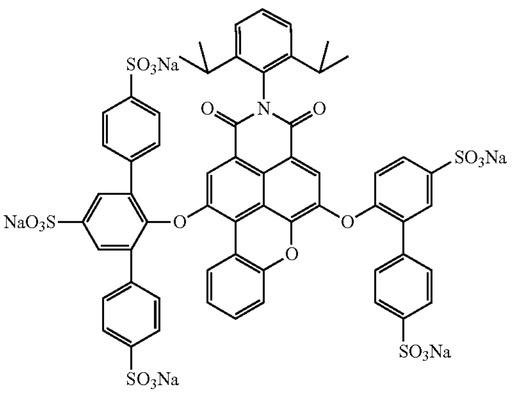
8-4
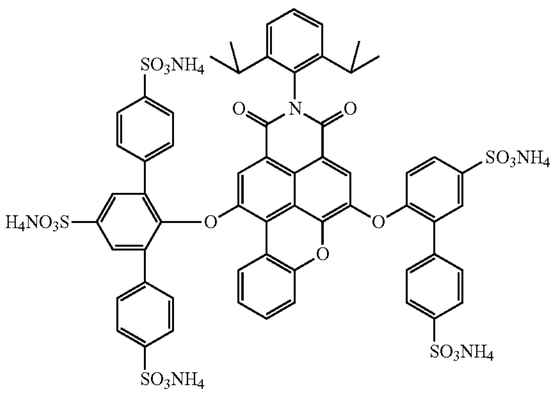
8-5
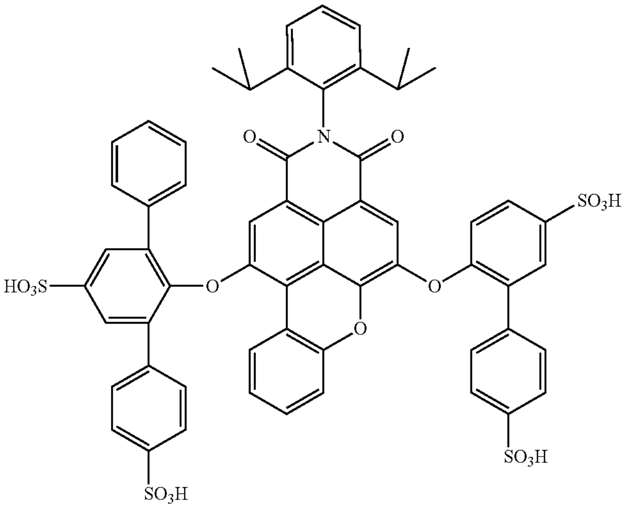

-continued
[Chem. 50]
8-6
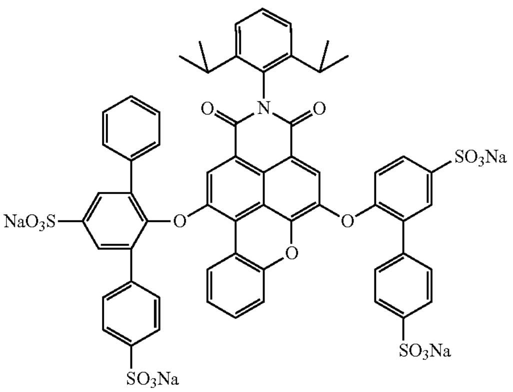
8-7
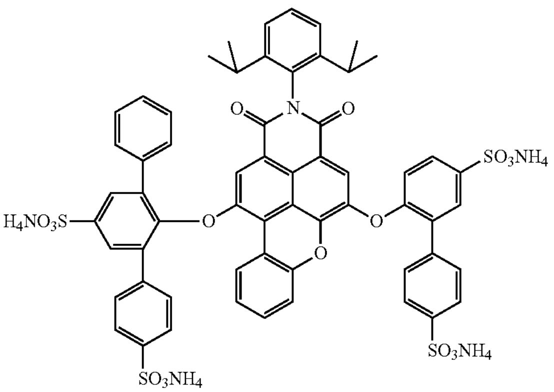
8-8
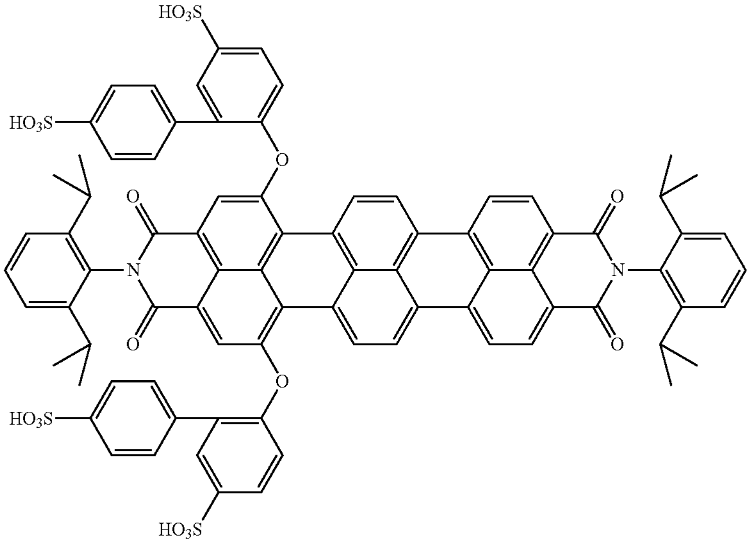
[Chem. 51]
8-9
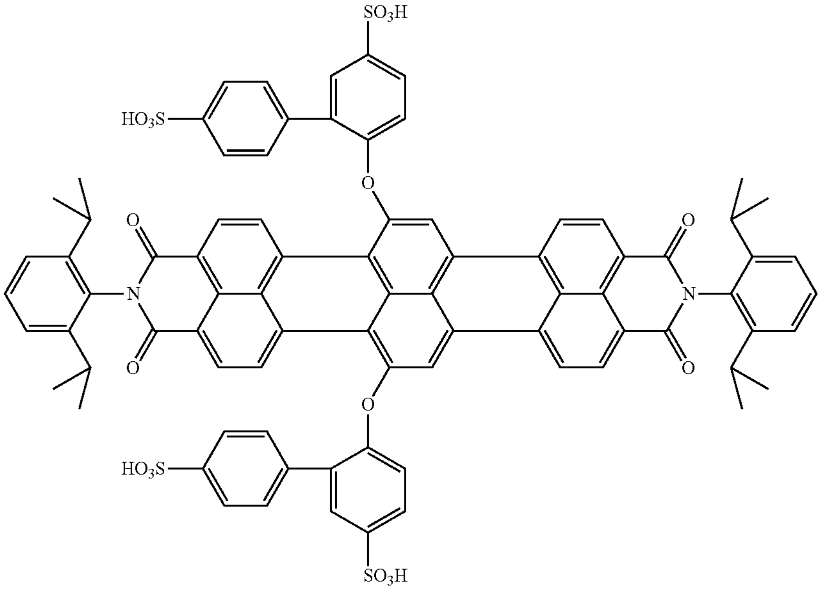

-continued
8-10
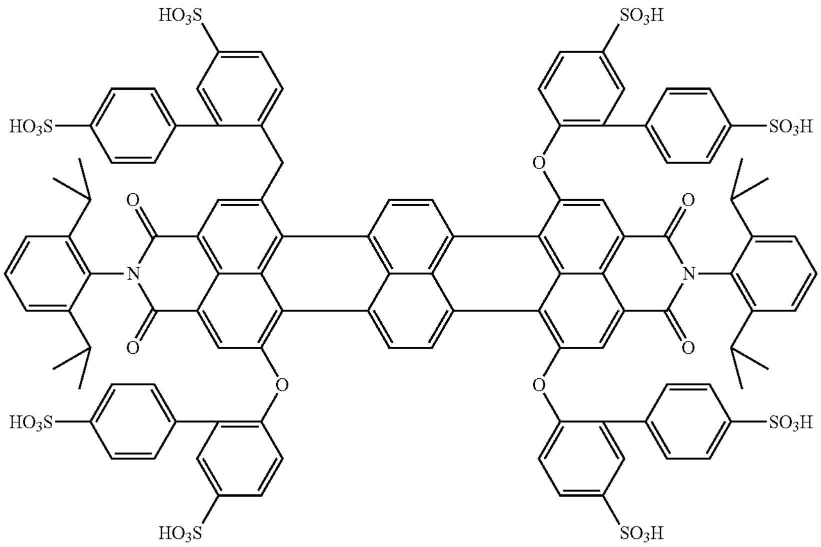
[Chem. 52]
8-11
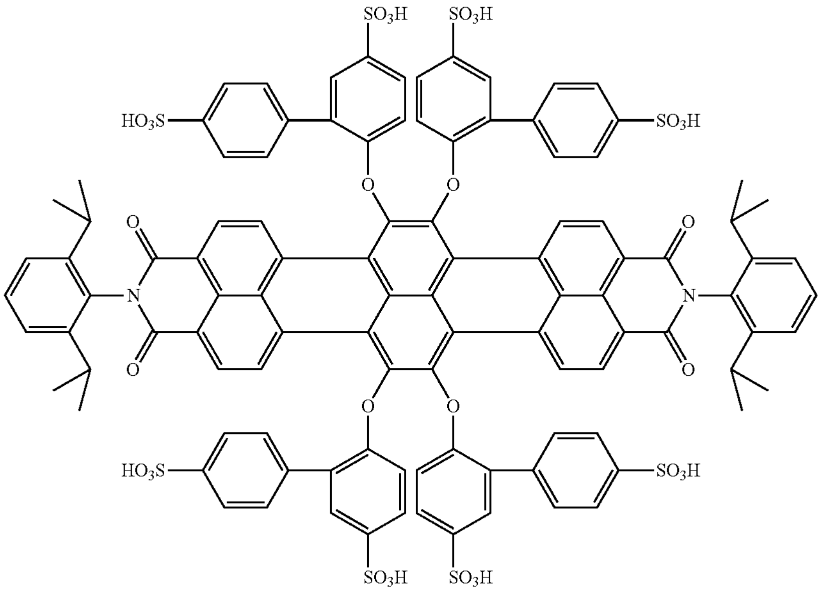

-continued
8-12
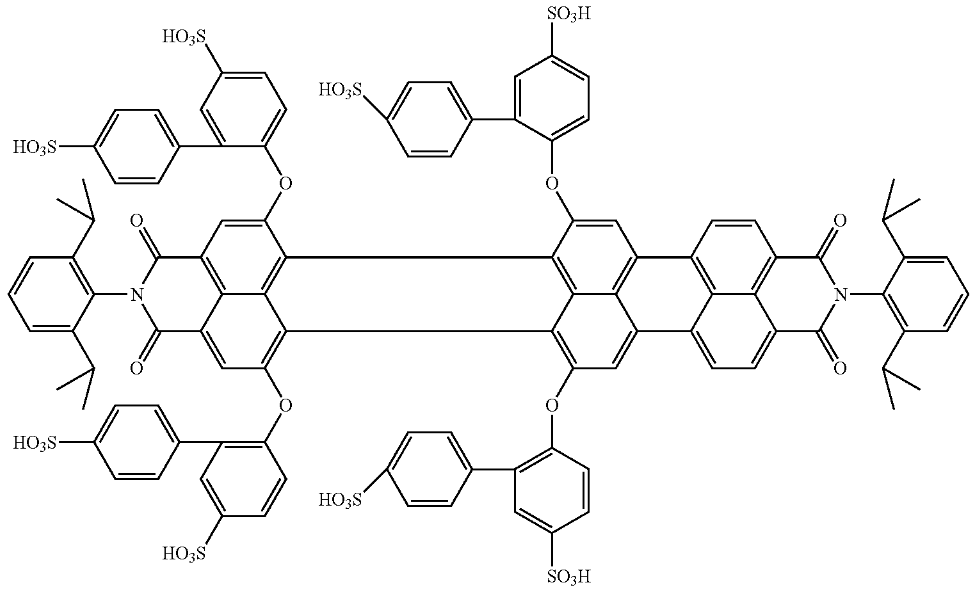
[Chem. 53]
8-13
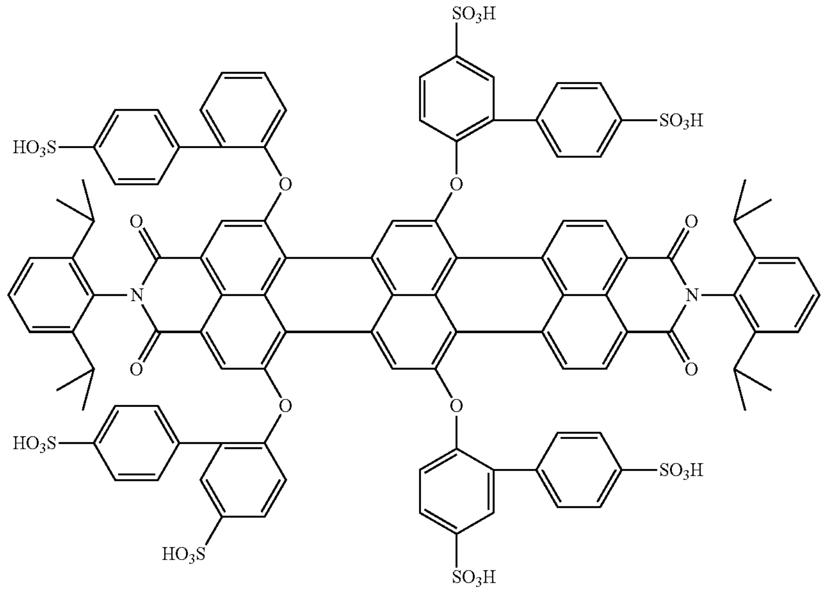

-continued
8-14
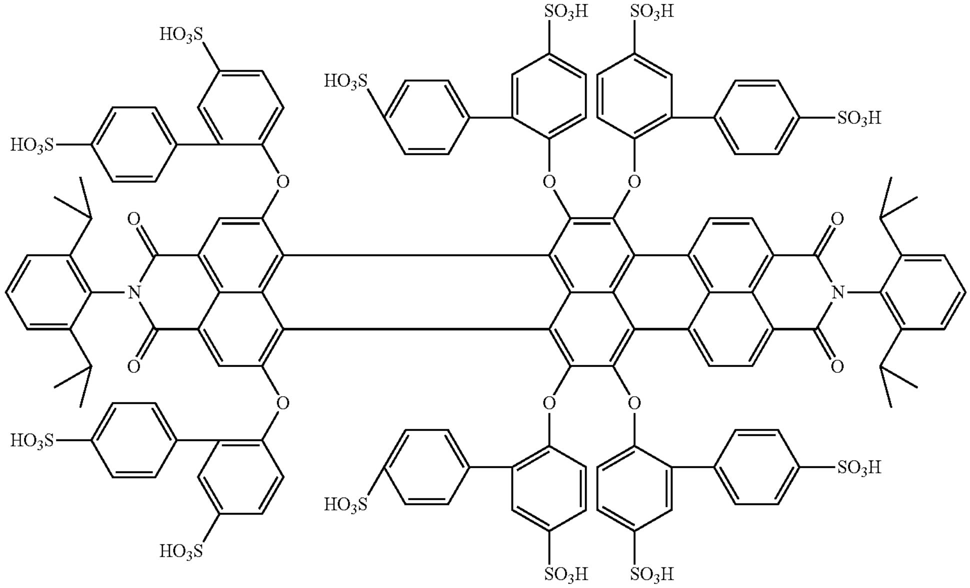
[Chem. 54]
8-15
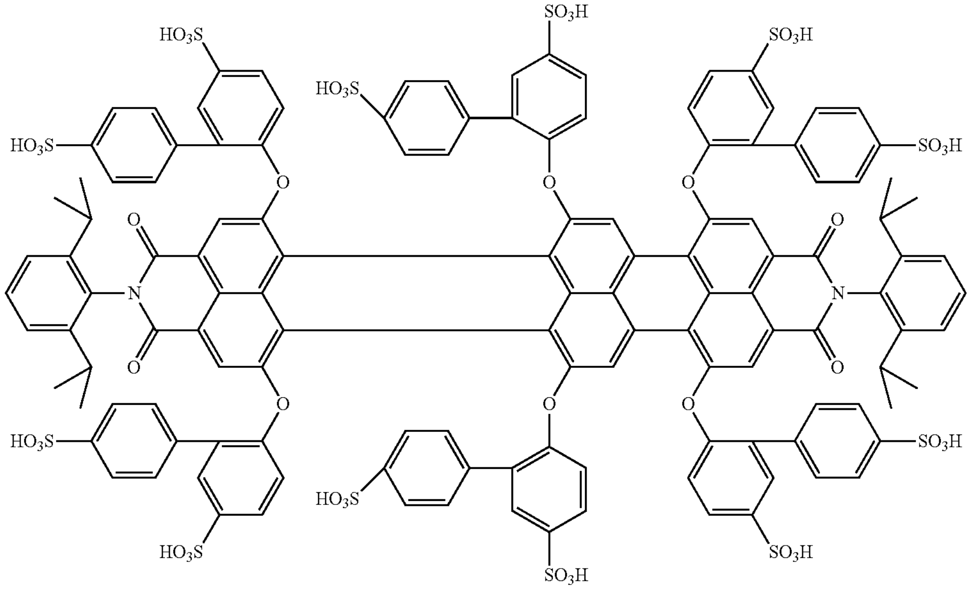

-continued 8-16

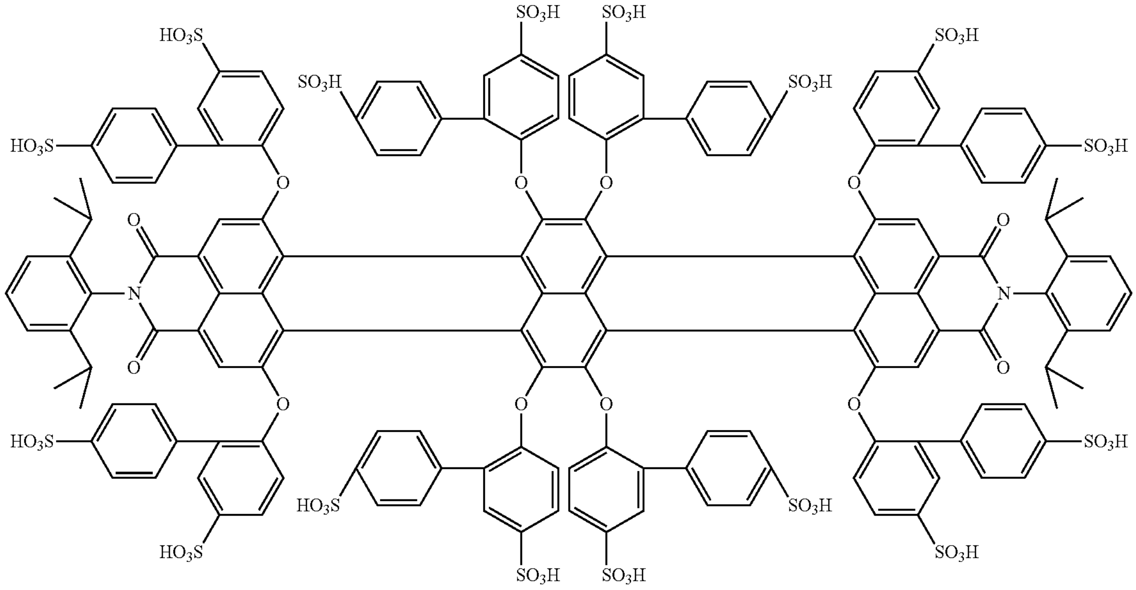

[Method for Producing the Luminescent Compound]

In the method for producing the luminescent compound according to the present invention, one sulfo group is introduced into each benzene ring by sulfonation of a dye molecule having a 2-biphenyloxy group(s). Thus, substitution with a plurality of ionic substituents can be performed at a time, leading to excellent production efficiency.

[Chem. 55]

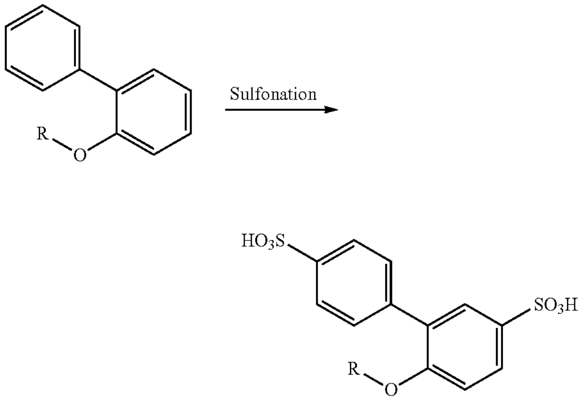

[In the formula, R represents a luminescent dye skeleton.]

In the formula, R has the same meaning as R in the general formula (1).

Synthesis Example of Exemplary Compound 1-1

The synthesis scheme of the Exemplary Compound 1-1 will be illustrated below. Detailed synthesis methods will be described in the Examples. Other exemplary compounds can be synthesized in the same manner. In the synthesis scheme, NMP represents N-methyl-2-pyrrolidone.

[Chem. 56]

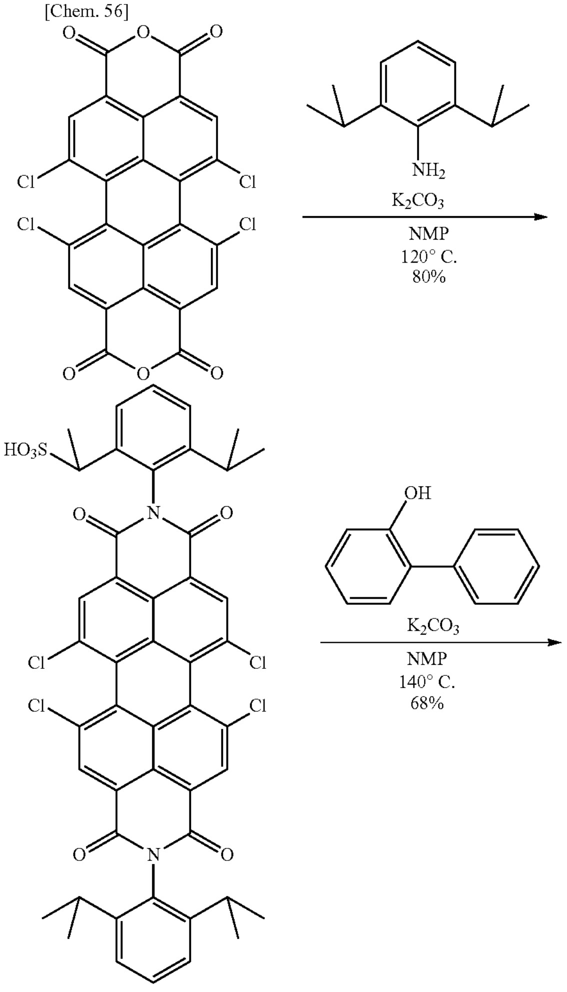

Intermediate 1

-continued

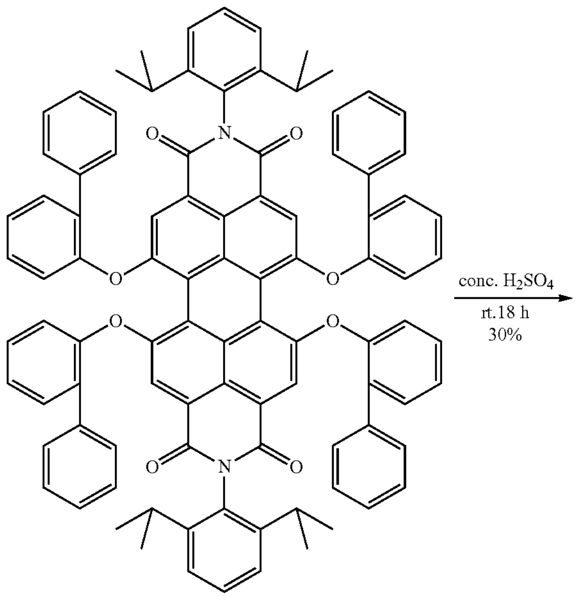

Intermediate 2

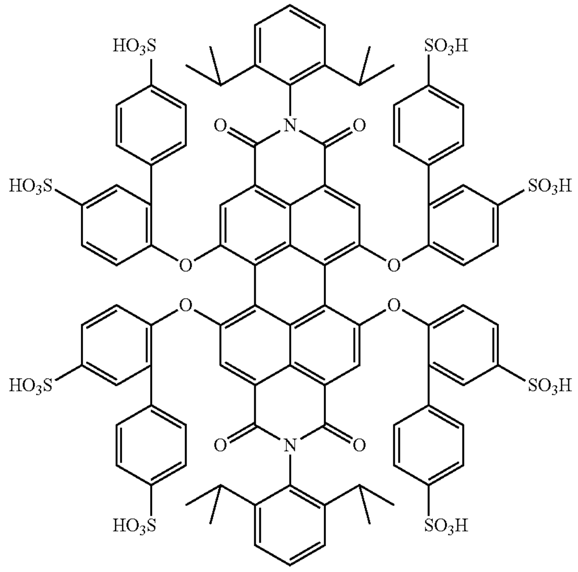

1-1

<Luminescence Quantum Yield>

The luminescence quantum yield is represented by the ratio between the number of absorbed photons and the number of emitted photons. In a case where all of the excited molecules emit fluorescence and return to the ground state, the luminescence quantum yield is 1, but is not actually 1 due to non-radiative deactivation.

Non-radiative deactivation is a transition returning to a ground state without emitting fluorescence, and includes relaxation to a triplet state by intersystem crossing, internal conversion in which energy in an electronic state is converted into vibrational energy or the like and finally becomes thermal energy, energy transfer in which energy is transferred to another molecule, and the like.

In a case where rate constants of fluorescence transition and non-radiative transition of a molecule in an excited state are represented by Kf and Knr, respectively, the luminescence quantum yield Φ (%) is represented as follows.

$$\Phi(\%)=(Kf/(Kf+Knr))\times 100$$

Therefore, in order to improve the luminescence quantum yield, it is necessary to suppress the non-radiative deactivation of molecules in an excited state.

In order for the non-radiation deactivation to be suppressed, the luminescent compound according to one or more embodiments of the present invention has an ionic substituent. The interaction between the fat-soluble dye cores is suppressed by the electrostatic repulsion by the ionic substituents, and the aggregation between the molecules is suppressed. As a result, it is assumed that quenching due to the aggregation becomes smaller and the luminescence property is improved.

(Measurement of Luminescence Quantum Yield)

In the luminescent compound of one or more embodiments of the present invention, concentration quenching is suppressed not only in a dilute solution but also in a high-concentration solution or film state, and a high luminescence quantum yield can be exhibited.

<Measurement of Luminescence Quantum Yield in the State of Solution>

The luminescence quantum yield of the solution-state luminescent compound can be measured by dissolving the luminescent compound in 2-methyltetrahydrofuran, measuring an absolute fluorescence quantum yield using, for example, a fluorescence quantum yield measuring device (C11347-01 manufactured by Hamamatsu Photonics K.K), and using the absolute fluorescence quantum yield as the luminescence quantum yield.

<Measurement of Luminescence Quantum Yield in Film State>

The luminescent compound of one or more embodiments of the present invention is ultrasonically washed with isopropyl alcohol and dried with dry nitrogen gas. Thereafter, chlorobenzene solutions of respective compounds are each added dropwise to a silica substrate (1 cm square) which has been subjected to UV ozone cleaning treatment and heated to 150° C. on a hotplate, and baked at 150° C. for 30 minutes, thereby preparing a single film of the luminescent compound. The absolute fluorescence quantum yield of this single film is measured using a fluorescence quantum yield measuring device (C11347-01 manufactured by Hamamatsu Photonics K.K) in a nitrogen atmosphere, and this can be used as the luminescence quantum yield.

[Use]

In the luminescent compound of one or more embodiments of the present invention, concentration quenching is suppressed not only in a dilute solution but also in a high-concentration solution or in a film state, and a high luminescence quantum yield can be exhibited. Having such properties, the luminescent compound of one or more embodiments of the present invention can be used as a luminescent composition, a luminescent thin film, or a luminescent particle.

For example, the luminescent compound of one or more embodiments of the present invention can be applied to an organic electronic device such as an organic electroluminescent element as a high-efficiency luminescent material. In addition, the luminescent compound of one or more embodiments of the present invention can be used for bioimage as a label in biology and medicine as a new type of dye for a fluorescent probe. The luminescent compound of one or more embodiments of the present invention, which emits fluorescence as excess energy when excited electrons return to the ground state, has a wavelength conversion ability due to a difference between absorption energy and emission energy, and can be used as a color conversion filter for dyes, pigments, optical filters, agricultural films, and the like.

[Luminescent Composition and Luminescent Thin Film]

The luminescent composition of one or more embodiments of the present invention contains the luminescent compound of one or more embodiments of the present invention. The luminescent composition of one or more embodiments of the present invention may be used as a composition obtained by adding a dispersant to the luminescent compound for film formation stability or the like, or a composition obtained by further adding a solvent to the above composition. Furthermore, the luminescent thin film of one or more embodiments of the present invention contains the luminescent compound of one or more embodiments of the present invention. Specifically, the luminescent thin film of one or more embodiments of the present invention can be prepared by forming the luminescent composition of one or more embodiments of the present invention into a thin film form.

Examples of the dispersant include a (meth)acrylate-based resin, a polyester-based resin, a polyamide-based resin, a polyimide-based resin, a polystyrene-based resin, a polyepoxy-based resin, a polyester-based resin, an amino-based resin, a fluorine-based resin, a phenol-based resin, a polyurethane-based resin, a polyethylene-based resin, a polypropylene-based resin, a polyvinyl chloride-based resin, a polyvinyl alcohol-based resin, a polyether-based resin, a polyether ketone-based resin, a polyphenylene sulfide resin, a polycarbonate-based resin, and an aramid resin, and a polystyrene-based resin, a polyethylene-based resin, a polypropylene-based resin, and a polyvinyl chloride-based resin may be preferable. In addition, copolymers thereof may be also preferable.

The (meth)acrylate-based resin is synthesized by homopolymerizing or copolymerizing various methacrylate-based monomers or acrylate-based monomers. A desired (meth)acrylate-based resin can be obtained by variously changing the monomer species and the monomer composition ratio. In addition, in one or more embodiments of the present invention, a copolymer of a (meth)acrylate-based monomer and a copolymerizable monomer having an unsaturated double bond other than the (meth)acrylate-based monomer can also be used. Furthermore, in one or more embodiments of the present invention, together with the poly (meth)acrylate-based resin, a plurality of other resins may be mixed for use.

Examples of the monomer component forming the (meth) acrylate-based resin used in one or more embodiments of the present invention include (meth)acrylic acid, methyl (meth) acrylate, ethyl (meth)acrylate, propyl (meth)acrylate, butyl (meth)acrylate, isopropyl (meth)acrylate, isobutyl (meth) acrylate, t-butyl (meth)acrylate, stearyl (meth)acrylate, 2-hydroxyethyl (meth)acrylate, acetoacetoxyethyl (meth) acrylate, dimethylaminoethyl (meth)acrylate, 2-hydroxypropyl (meth)acrylate, di (ethylene glycol)ethyl ether (meth) acrylate, ethylene glycol methyl ether (meth)acrylate, isobornyl (meth)acrylate, ethyltrimethylammonium chloride (meth)acrylate, trifluoroethyl (meth)acrylate, octafluoropentyl (meth)acrylate, 2-acetamidomethyl (meth) acrylate, 2-methoxyethyl (meth)acrylate, 2-dimethylaminoethyl (meth)acrylate, 3-trimethoxysilylpropyl (meth) acrylate, benzyl (meth) acrylate, tridecyl (meth)acrylate, 4-hydroxybutyl (meth) acrylate, tetrahydrofurfuryl (meth)acrylate, dodecyl (meth)acrylate, octadecyl (meth)acrylate, 2-diethylaminoethyl (meth)acrylate, 2-ethylhexyl (meth)acrylate, cyclohexyl (meth)acrylate, phenyl (meth)acrylate, and glycidyl (meth)acrylate, and preferred examples thereof may include (meth)acrylic acid, methyl (meth)acrylate, ethyl (meth)acrylate, propyl (meth)acrylate, butyl (meth) acrylate, stearyl (meth)acrylate, 2-hydroxyethyl (meth)acrylate, acetoacetoxyethyl (meth)acrylate, benzyl (meth)acrylate, tridecyl (meth)acrylate, dodecyl (meth)acrylate, and 2-ethylhexyl (meth)acrylate.

Examples of the polystyrene-based resin include a homopolymer of a styrene monomer and a random copolymer, a block copolymer, and a graft copolymer obtained by copolymerizing a styrene monomer and another monomer having an unsaturated double bond which is copolymerizable with the styrene monomer. Furthermore, the polystyrene-based resin includes a blend or a polymer alloy in which the polymer is blended with another polymer. Examples of the styrene monomer include styrene, a nuclear alkyl-substituted styrene such as α-methylstyrene, α-ethylstyrene, α-methylstyrene-p-methylstyrene, o-methylstyrene, m-methylstyrene, and p-methylstyrene, and a nuclear halogenated styrene such as o-chlorostyrene, m-chlorostyrene, p-chlorostyrene, p-bromostyrene, dichlorostyrene, dibromostyrene, trichlorostyrene, and tribromostyrene. Among these, styrene and α-methylstyrene may be preferable.

Examples of the resin used in one or more embodiments of the present invention by homopolymerizing or copolymerizing these include a copolymer resin such as benzyl methacrylate/ethyl acrylate or butyl acrylate, a copolymer resin such as methyl methacrylate/2-ethylhexyl methacrylate, a copolymer resin of methyl methacrylate/methacrylic acid/stearyl methacrylate/acetoacetoxyethyl methacrylate, a copolymer resin of styrene/acetoacetoxyethyl methacrylate/stearyl methacrylate, a copolymer of styrene/2-hydroxyethyl methacrylate/stearyl methacrylate, and a copolymer resin such as 2-ethylhexyl methacrylate/2-hydroxyethyl methacrylate.

The lower limit of the content of the luminescent compound in the luminescent composition and the luminescent thin film according to one or more embodiments of the present invention may be 0.001 parts by mass, and the upper limit thereof may be 50 parts by mass, relative to 100 parts by mass of the dispersant. When the content of the luminescent compound is within this range, the luminescent compound and the luminescent thin film have high transparency and can display an image with high luminance by irradiation with light rays. The lower limit of the content of the luminescent compound may be 0.01 parts by mass, the upper limit may be 10 parts by mass, the lower limit may be 0.05 parts by mass, the upper limit may be 8 parts by mass, the lower limit may be 0.1 parts by mass, and the upper limit may be 5 parts by mass.

Furthermore, the luminescent thin film of one or more embodiments of the present invention can be used appropriately within the range of 0.1 nm to 1 mm in thickness.

[Luminescent Particle]

The luminescent particle of one or more embodiments of the present invention contains the luminescent compound of one or more embodiments of the present invention. The luminescent particle according to one or more embodiments of the present invention may be a luminescent particle on a surface of which the luminescent compound is adsorbed or a luminescent particle encapsulating the luminescent compound.

For example, the luminescent particles according to one or more embodiments of the present invention can be prepared by aggregating the luminescent compound in a polymer particle dispersion. Furthermore, the luminescent particle of one or more embodiments of the present invention may be a luminescent particle encapsulating the luminescent compound using a swellable polymer whose volume expands due to absorption of a solvent by a polymer particle when the polymer particle is immersed in the solvent.

As the polymer particles, commercially available products may be used, or those synthesized by conventionally known methods may be used. The conventionally known method is not particularly limited, and examples thereof include a dispersion polymerization method, a suspension polymerization method, and an emulsion polymerization method, of which the emulsion polymerization method may be preferable. As a monomer which is a raw material of the polymer, various monomers exemplified in the description of the dispersant can be used.

Furthermore, the solvent in the case of aggregating the luminescent compound in the polymer dispersion is not particularly limited, and known solvents can be used.

The volume average particle diameter of the polymer particle may be in the range of 0.01 to 50 μm, may be 0.02 to 40 μm, or may be 0.04 to 20 μm.

When the volume average particle diameter is within the above range, the obtained luminescent particle can be applied to various uses. Specifically, the volume average particle diameter can be measured with a laser diffraction scattering light particle size distribution measuring apparatus, Type LS13320.

The weight-average molecular weight of the polymer particle may be in a range of 1000 to 1000,000, may be in a range of 5000 to 800000, and may be in a range of 10000 to 600000.

The polymer particle contained in the luminescent particle according to one or more embodiments of the present invention may be of one type or two or more types, but are usually of one type.

[Organic Electroluminescent Element]

An organic electroluminescent element (organic EL element) is an element which has a configuration in which a light emitting layer containing a compound which emits light (luminescent material) is sandwiched between a cathode and an anode on a substrate, in which electrons and holes are injected into the light emitting layer and recombined to generate excitons, and in which luminescence when the excitons are deactivated is utilized to emit light. The luminescent compound of one or more embodiments of the present invention can be applied to an organic EL element as a fluorescent emitting material.

One or more specific examples of the layer configuration of the organic EL element are shown below.

(i) anode/light-emitting layer/electron transport layer/cathode (ii) anode/hole transport layer/light-emitting layer/electron transport layer/cathode (iii) anode/hole transport layer/light-emitting layer/hole blocking layer/electron transport layer/cathode (iv) anode/hole transport layer/light-emitting layer/hole blocking layer/electron transport layer/cathode buffer layer/cathode (v) anode/anode buffer layer/hole transport layer/light-emitting layer/hole blocking layer/electron transport layer/cathode buffer layer/cathode Here, the hole transport layer includes the concepts of a hole injection layer and an electron blocking layer.

The light-emitting layer is a layer in which electrons and holes injected from an electrode, an electron transport layer, or a hole transport layer are recombined to emit light, and a portion that emits light may be within the light-emitting layer or at an interface between the light-emitting layer and an adjacent layer. The luminescent compound of one or more embodiments of the present invention can be used in the light-emitting layer. Since concentration quenching is small, a high luminescence quantum yield can be realized even in the form of a film.

Furthermore, when the luminescent compound of one or more embodiments of the present invention is used as the luminescent material of the organic EL element, a known host compound as the dispersant can be used. Specific examples thereof include compounds described in the following literatures, but one or more embodiments of the present invention is not limited thereto. JP2001-257076A, JP2002-308855A, JP2001-313179A, JP2002-319491A, JP2001-357977A, JP2002-334786A, JP2002-8860A, JP2002-334787A, JP2002-15871A, JP2002-334788A, JP2002-43056A, JP2002-334789A, JP2002-75645A, JP2002-338579A, JP2002-105445A, JP2002-343568A, JP2002-141173A, JP2002-352957A, JP2002-203683A, JP2002-363227A, JP2002-231453A, JP2003-3165A, JP2002-234888A, JP2003-27048A, JP2002-255934A, JP2002-260861A, JP2002-280183A, JP2002-299060A, JP2002-302516A, JP2002-305083A, JP2002-305084A, JP2002-308837A, US2003/0175553A1, US2006/0280965A1, US2005/0112407A1, US2009/0017330A1, US2009/0030202A1, US2005/0238919A1, WO2001/039234A2, WO2009/021126A2, WO2008/056746A1, WO2004/093207A2, WO2005/089025A1, WO2007/063796A1, WO2007/063754A1, WO2004/107822A1, WO2005/030900A1, WO2006/114966A1, WO2009/086028A2, WO2009/003898A1, WO2012/023947A1, JP2008-074939A, JP2007-254297A, EP2034538A1, WO2011/055933A2, WO2012/035853A1, JP2015-38941A, and the like.

For the light-emitting layer, known materials such as other fluorescent light emitting materials and phosphorescent light emitting materials can be used in combination.

The charge injection layer is a layer provided between the electrode and the light-emitting layer in order to reduce the driving voltage and improve the emission luminance, and includes a hole injection layer and an electron injection layer.

The hole transport layer is composed of a hole transport material having a function of transporting holes, and in a broad sense, the hole injection layer and the electron blocking layer also have the function of the hole transport layer. The hole transport layer can be provided as a single layer or a plurality of layers.

The electron transport layer is composed of a material having the function of transporting electrons, and an electron injection layer and a hole blocking layer are also included in the electron transport layer in a broad sense. The electron transport layer can be provided as a single-layer structure or a stacked structure of a plurality of layers.

The blocking layer includes a hole blocking layer and an electron blocking layer, and is a layer provided as necessary in addition to each of the constituent layers of the organic functional layers described above.

Known materials can be used for the substrate, the electrode, the charge injection layer, the hole transport layer, the electron transport layer, the blocking layer, and the like.

[Bioimage]

The luminescent compound according to one or more embodiments of the present invention can be used as a fluorescent dye. In a case where the luminescent compound according to one or more embodiments of the present invention is applied to bioimage, by staining a living cell with a fluorescent dye and then examining the emission color of the stained cell, it is possible to know the environment around the cell from the emission color and to image the intracellular environment.

For example, in order to know the expression state of a target biological substance, a technique of performing fluorescent labeling using fluorescent substance-integrated nanoparticles to which a biological substance-recognition site capable of recognizing and binding to the target biological substance is bound is known. Specifically, the expression level of the target biological substance can be evaluated by staining a tissue specimen with the fluorescent substance-integrated nanoparticles, analyzing the peak of the luminance distribution of fluorescence emission bright points to obtain an average luminance value per particle, calculating the number of particles in each bright point, and comparing the calculated number of particles.

Since the luminescent compound according to one or more embodiments of the present invention has a high luminescence quantum yield, the luminance value per particle of the fluorescent substance-integrated nanoparticle can be increased. Therefore, when applied to such bioimage, it has an advantage that a trace amount of a biological substance can be quantitatively detected.

[Color Conversion Filter]

The color conversion filter can be used for, for example, image display devices such as a liquid crystal display device (LCD), a plasma display panel (PDP), an electroluminescent display (ELD), a cathode ray tube display device (CRT), a fluorescent display tube, and a field emission display, and lighting devices such as LED lighting and electroluminescent lighting. In a case where the color conversion filter is used in an image display device, correction to a preferable hue can be performed without reducing display luminance, and in a case where the color conversion filter is used in a lighting device (particularly, LED lighting), white light that is felt more natural can be obtained.

The color conversion filter may be the same as a conventional optical filter except that it contains at least one luminescent compound of one or more embodiments of the present invention which emits fluorescence, and its configuration is not limited. The color conversion filter has, for example, at least a support as in the conventional one, and can have various functional layers such as an optical functional layer, an undercoat layer, an antireflection layer, a hard coat layer, and a lubricating layer as necessary. In the color conversion filter, the luminescent compound according to one or more embodiments of the present invention that emits fluorescence may be contained in any of the support or various functional layers, and may be contained in the support or the optical functional layer. In addition, the size and shape of the color conversion filter are not particularly limited, and are appropriately determined according to the use.

EXAMPLE

Hereinafter, one or more embodiments of the present invention will be described in detail with reference to examples, but the present invention is not limited thereto. Note that, in the following examples, operations were performed at room temperature (25° C.) unless otherwise specified. Furthermore, unless otherwise specified, "%" and "part(s)" mean "mass %" and "part(s) by mass", respectively.

[Synthesis of Exemplary Compound 1-1 of Present Invention]

The Exemplary Compound 1-1 according to one or more embodiments of the present invention was synthesized according to the synthesis procedure described below.

2,6-diisopropylaniline and propionic acid were added to 1,6,7,12-tetrachloroperylenetetracarboxylic dianhydride (product number W01COBQA-7294, manufactured by FUJIFILM Wako Pure Chemical Corporation), and the mixture was refluxed in a solvent for 3 hours to be reacted. The reaction product was purified by using silica gel column chromatography, and an intermediate 1 was obtained as an orange solid (yield 80%).

Next, the obtained intermediate 1 was dissolved in N-methylpyrrolidone (NMP) and reacted with 2-phenylphenol added thereto under the presence of potassium carbonate ($K_2CO_3$) at 140° C. for 18 hours. The reaction product was purified by using silica gel column chromatography, and an intermediate 2 was obtained as a dark red solid (yield 68%).

Next, the intermediate 2 and an excess of concentrated sulfuric acid were reacted at room temperature for 2 days. The reaction product was purified by using medium pressure reverse phase column chromatography, and the Exemplary Compound 1-1 according to one or more embodiments of the present invention was obtained as a dark purple solid (yield: 30%).

The synthesis scheme is shown below.

[Chem. 57]

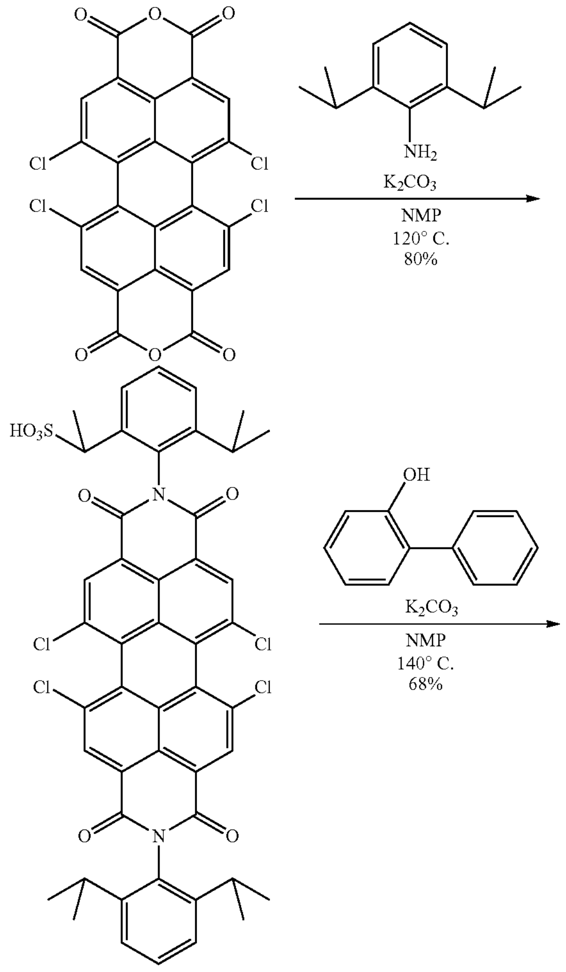

Intermediate 1

-continued

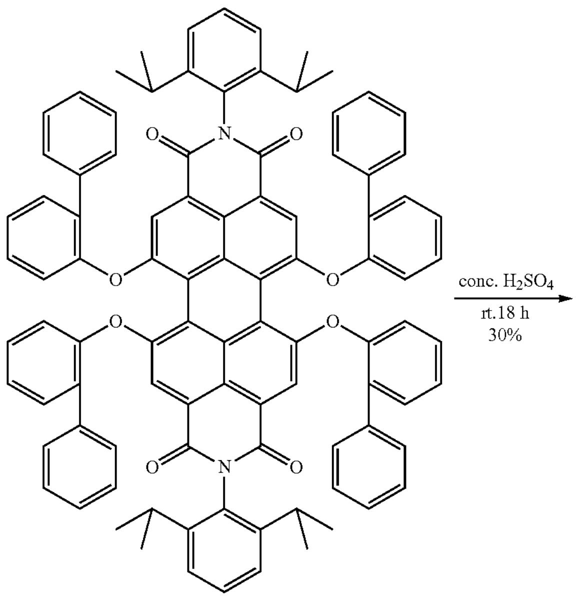

Intermediate 2

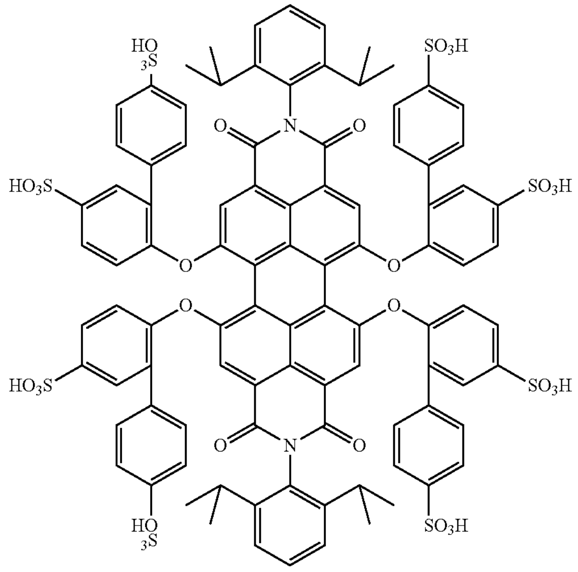

1-1

The structures of Comparative Compound 1 and Comparative Compound 2 used in Comparative Examples are shown below.

[Chem. 58]

Comparative Compound 1

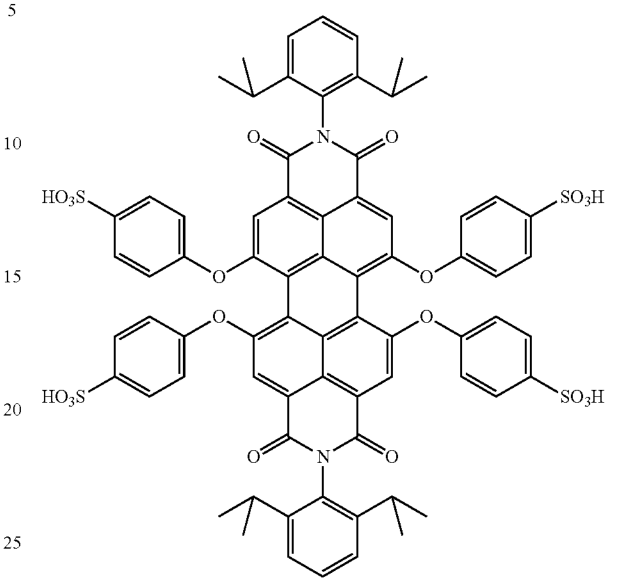

Comparative Compound 2

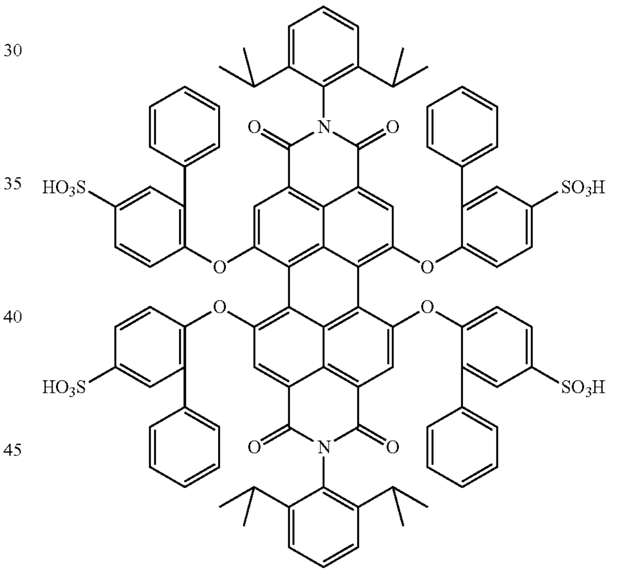

[Evaluation of Luminescence Quantum Yield in Doped Film State]

The synthesized Exemplary Compound 1-1 according to one or more embodiments of the present invention was subjected to ultrasonic cleaning with isopropyl alcohol, and dried with dry nitrogen gas. Thereafter, a solution of the Exemplary Compound 1-1 and a poly methyl methacrylate (PMMA) in propylene glycol monomethyl ether (PGME) was dropped onto a UV-ozone washed quartz substrate (1 cm square), and a film was formed by spin coating. The absolute fluorescence quantum yield was measured in a nitrogen atmosphere using the fluorescence quantum yield measuring device (C11347-01 manufactured by Hamamatsu Photonics K.K), and this was taken as the luminescence quantum yield in the doped film state.

The quantum yield in a case where the dye doping concentration was 1% was set to 1, and FIG. 1 shows a change in quantum yield in a case where the doping concentration was increased.

The absolute fluorescence quantum yield of each of Comparative Compound 1 and Comparative Compound 2 was measured in the same manner, and the change in quantum yield as the dye doping concentration was increased is shown in FIG. 1.

From the results shown in FIG. 1, it is found that the luminescent compound according to one or more embodiments of the present invention (Exemplary Compound 1-1) has an excellent luminescent properties because concentration quenching due to an increase in the doping concentration can be suppressed, as compared with Comparative Compound 1 and Comparative Compound 2.

Example 2

<Preparation of Luminescent Particle>

The synthesized luminescent compound (Exemplary Compound 1-1) according to one or more embodiments of the present invention was added to 22 mL of water and dissolved. Thereafter, 2 mL of a 5% aqueous solution of Emulsion® 430 (polyoxyethyleneoleyl ether, manufactured by Kao Corporation), an emulsifier for emulsion polymerization, was added to the solution. After the solution was heated to 70° C. with stirring on a hot stirrer, 0.65 g of NIKALAC MX-035 (manufactured by Nippon Carbide Industries Co., Inc.), a melamine resin raw material, was added thereto.

Furthermore, to this solution, 1000 μL of a 10% aqueous solution of dodecylbenzenesulfonic acid (manufactured by Kanto Chemical Co., Inc.) as a surfactant was added, and the mixture was heated and stirred at 70° C. for 50 minutes. Thereafter, the temperature was raised to 90° C., and the mixture was heated and stirred for 20 minutes. In order for impurities such as excess resin raw material and fluorescent dye to be removed from the obtained dispersion of the dye resin particles, washing with pure water was performed.

Specifically, centrifugation was performed for 15 minutes at 20000 G using a centrifuge (Micro Refrigerated Centrifuge Model 3740 manufactured by Kubota Corporation), the supernatant was removed, ultrapure water was added thereto, ultrasonic irradiation was performed, and redispersion was performed. Washing including centrifugation, removal of supernatant, and redispersion in ultrapure water was repeated 5 times. The absolute fluorescence quantum yield of the obtained aqueous dispersion of the fluorescent particles was measured using the fluorescence quantum yield measuring device (C11347-01, manufactured by Hamamatsu Photonics K.K), and this was taken as the luminescence quantum yield of the luminescent particles.

With respect to the above-described Comparative Compound 1 and Comparative Compound 2, preparation of luminescent particles and measurement of the luminescence quantum yield were performed in the same manner.

The amount of the dye was adjusted so that the concentration of the dye in the particle was 20%, and the luminescence quantum yield of the prepared luminescent particle is shown in Table I.

TABLE I

| Compound | Luminescence Quantum Yield [%] | Remarks |
|---|---|---|
| Exemplary Compound 1-1 | 28 | Present Invention |
| Comparative Compound 1 | 10 | Comparative Example |
| Comparative Compound 2 | 9 | Comparative Example |

From the results shown in Table I, it can be seen that the concentration quenching accompanying an increase in the doping concentration of the luminescent compound of one or more embodiments of the present invention (Exemplary Compound 1-1) can be suppressed as compared with those at of Comparative Compounds 1 and 2. Further, it can be seen that the luminescent compound of one or more embodiments of the present invention (Exemplary Compound 1-1) is superior in luminescence to Comparative Compound 1 and Comparative Compound 2.

INDUSTRIAL APPLICABILITY

One or more embodiments of the present invention can be used for a luminescent compound, a method for producing the luminescent compound, a luminescent composition, a luminescent thin film, and a luminescent particle having high water solubility and excellent luminescence even under a high concentration condition due to the concentration quenching suppressing effect.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A luminescent compound having a structure represented by a general formula (1), General formula (1)

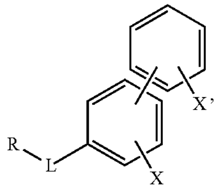

wherein R represents a luminescent dye skeleton, X represents an ionic substituent, and L represents a single bond, an oxygen atom, a sulfur atom, a selenium atom, or an NH group.

2. The luminescent compound according to claim 1, wherein the structure represented by the general formula (1) has a structure represented by a general formula (2), General formula (2)

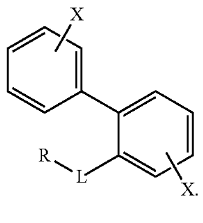

3. The luminescent compound according to claim 1, wherein the luminescent dye skeleton represented by R in the general formula (1) comprises a structure represented by one of cores,

R =

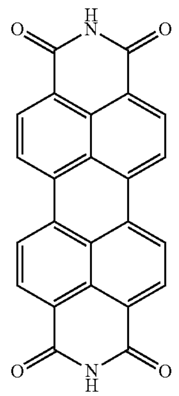

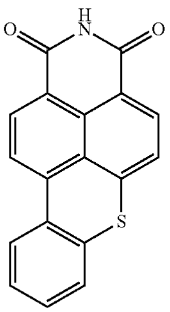

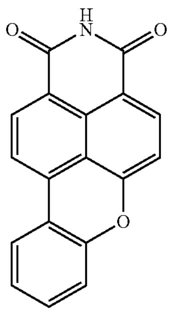

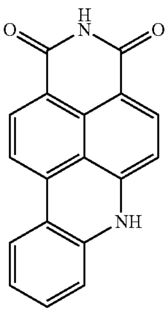

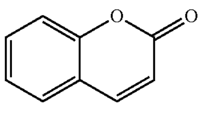

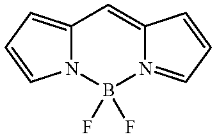

-continued

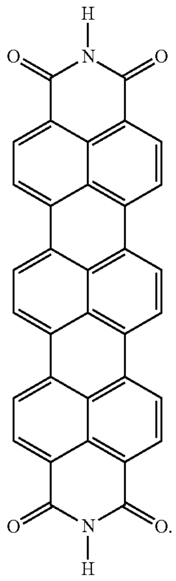

4. The luminescent compound according to claim 1, wherein, in the general formula (1), the ionic substituent represented by X is a sulfo group, a phosphoric acid group, a sulfonic acid ester group, a phosphoric acid ester group, an ammonium group, or a salt thereof.

5. The luminescent compound according to claim 1, wherein, in the general formula (1), L is an oxygen atom.

6. The luminescent compound according to claim 1, wherein, in the general formula (1), the ionic substituent represented by X is a sulfo group or a salt thereof.

7. A method for producing a luminescent compound of claim 1, comprising:

introducing one sulfo group into each benzene ring by sulfonation of a dye molecule having a 2-biphenyloxy group, wherein the sulfonation is represented by:

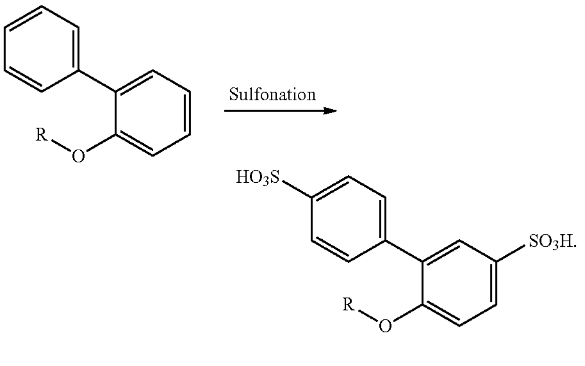

8. A luminescent composition comprising the luminescent compound according to claim 1.

9. A luminescent thin film, comprising the luminescent compound according to claim 1.

10. A luminescent particle comprising the luminescent compound according to claim 1.

* * * * *